(12) United States Patent
Akimoto et al.

(10) Patent No.: US 9,824,445 B2
(45) Date of Patent: Nov. 21, 2017

(54) ENDOSCOPE SYSTEM

(71) Applicant: OLYMPUS CORPORATION, Tokyo (JP)

(72) Inventors: Syunya Akimoto, Kawasaki (JP); Junichi Onishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/296,445

(22) Filed: Oct. 18, 2016

(65) Prior Publication Data

US 2017/0039707 A1 Feb. 9, 2017

Related U.S. Application Data

(63) Continuation of application No. PCT/JP2015/061634, filed on Apr. 15, 2015.

(30) Foreign Application Priority Data

Jun. 18, 2014 (JP) ................... 2014-125634

(51) Int. Cl.
*G06K 9/00* (2006.01)
*G06T 7/00* (2017.01)
(Continued)

(52) U.S. Cl.
CPC .............. *G06T 7/0012* (2013.01); *A61B 1/00* (2013.01); *A61B 1/00009* (2013.01);
(Continued)

(58) Field of Classification Search
CPC ... G06T 7/0012; G06T 7/0081; G06T 7/0085; G06T 2207/10012; G06T 2207/10068;
(Continued)

(56) References Cited

U.S. PATENT DOCUMENTS

2007/0182731 A1 8/2007 Gundel
2012/0053408 A1 3/2012 Miyamoto
2013/0257865 A1 10/2013 Kobayashi

FOREIGN PATENT DOCUMENTS

EP 2423877 A1 2/2012
JP 2007-195971 A 8/2007
(Continued)

OTHER PUBLICATIONS

Hayashi et al. "Quantitative evaluation of observation methods in virtual endoscopy based on the rate of undisplayed region", Feb. 15, 2003, SPIE, Proc. SPIE 5031, Medical Imaging 2003: Physiology and Function: Methods, Systems, and Applications, vol. 5031, p. 69-79.*

(Continued)

*Primary Examiner* — Stephen R Koziol
*Assistant Examiner* — Timothy Choi
(74) *Attorney, Agent, or Firm* — Scully, Scott, Murphy & Presser, P.C.

(57) ABSTRACT

An endoscope system for analyzing, when an endoscope is inserted into a subject, an observed region and an unobserved region of the endoscope using information of a three-dimensional image of the subject obtained in advance, including: one or more processors comprising hardware, for: three-dimensionally changing a display direction for displaying a luminal organ model extracted from a three-dimensional image, and when an identification image provided with identification information is generated on the luminal organ model with the display direction changed, generating the identification image in a direction such that a proportion of the non-angle-of-view region in the identification image is largest.

9 Claims, 15 Drawing Sheets

(51) Int. Cl.
  *A61B 1/00* (2006.01)
  *A61B 1/04* (2006.01)
  *G02B 23/24* (2006.01)
  *H04N 7/18* (2006.01)

(52) U.S. Cl.
  CPC ............ *A61B 1/00045* (2013.01); *A61B 1/04* (2013.01); *G02B 23/24* (2013.01); *G02B 23/2484* (2013.01); *G06T 7/0081* (2013.01); *G06T 7/0085* (2013.01); *H04N 7/18* (2013.01); *G06T 2207/10012* (2013.01); *G06T 2207/10068* (2013.01); *G06T 2207/10081* (2013.01); *G06T 2207/30004* (2013.01)

(58) Field of Classification Search
  CPC . G06T 2207/10081; G06T 2207/30004; A61B 1/00; A61B 1/00009; A61B 1/00045; A61B 1/04; G02B 23/24; G02B 23/2484; H04N 7/18
  See application file for complete search history.

(56) References Cited

FOREIGN PATENT DOCUMENTS

| | | |
|---|---|---|
| JP | 2011-036600 A | 2/2011 |
| JP | 2011-212242 A | 10/2011 |
| JP | 2012-050606 A | 3/2012 |
| JP | 2013-027697 A | 2/2013 |
| WO | WO 2012/176854 A1 | 12/2012 |

OTHER PUBLICATIONS

International Search Report dated Jul. 14, 2015 issued in PCT/JP2015/061634.
Japanese Office Action dated Mar. 15, 2016 issued in 2015-560465.
Hayashi, Yuichiro, "Development of automated navigation function in the Virtualized Endoscope System", The Institute of Electronics, Information and Communication Engineers Sogo Taikai Koen Ronbunshu, Mar. 7, 2000, vol. 2000, Sogo 7, pp. 411-412.

* cited by examiner

| OBSERVATION POSITION | VISUAL LINE DIRECTION | BOUNDARY POSITION | TIME PERIOD |
|---|---|---|---|
| P1 | D1 | B1 | t1 |
| P2 | D2 | B2 | t2 |
|  |  |  |  |

ENDOSCOPE SYSTEM

CROSS REFERENCE TO RELATED APPLICATION

This application is a continuation application of PCT/JP2015/061634 filed on Apr. 15, 2015 and claims benefit of Japanese Application No. 2014-125634 filed in Japan on Jun. 18, 2014, the entire contents of which are incorporated herein by this reference.

BACKGROUND OF THE INVENTION

1. Field of the Invention

The present invention relates to an image processing apparatus configured to execute image processing when an inside of a luminal organ of a subject is observed.

2. Description of the Related Art

In recent years, an endoscope configured to observe an inside of a subject has been widely used in a medical field and the like. The endoscope is inserted into luminal organs branched in a complicated manner, such as renal calyces of a kidney, and used for examination and observation of existence of a lesion or the like in some cases.

In a conventional example disclosed in Japanese Patent Application Laid-Open Publication No. 2013-27697, a virtualized endoscope configured to virtually perform endoscopic observation based on a viewpoint position set in a luminal organ is used to generate a virtualized endoscopic image, and an observed region and an unobserved region in the virtualized endoscope are obtained. The observed region and the unobserved region are displayed on an image obtained from a three-dimensional image of the luminal organ in a manner that the observed region and the unobserved region can be distinguished.

In the conventional example, the observed region provided with light on an inner wall of the luminal organ and the unobserved region not provided with the light are calculated when a light beam is virtually applied in a view angle of the virtualized endoscope at the viewpoint position and visual line direction set in the luminal organ. When the virtualized endoscope is moved for example, a similar process is executed at each of the moved viewpoint positions.

SUMMARY OF THE INVENTION

An aspect of the present invention provides an image processing apparatus including: an information acquisition section configured to acquire information of an observation position and a visual line direction for observing an inside of a subject by using an objective optical system; a boundary position generation section configured to generate boundary position information indicating a boundary position of an angle-of-view region and another region of the objective optical system on a three-dimensional image of the subject based on the information of the observation position and the visual line direction that change along with temporal change observation and based on angle of view information indicating an angle of view in observation using the objective optical system; a non-angle-of-view region extraction section configured to extract a non-angle-of-view region not in the angle of view on the three-dimensional image based on the boundary position information generated by the boundary position generation section; and an image generation section configured to generate an identification image for a luminal organ model based on the three-dimensional image, the identification image being provided with identification information for identifying the non-angle-of view region.

BRIEF DESCRIPTION OF THE DRAWINGS

FIG. 6A is an explanatory diagram of a situation of inserting the insertion portion into the renal pelvis and renal calyces to acquire data of a boundary position that is a boundary of an angle of view of an image pickup section;

FIG. 6B is a diagram showing, in a table format, an example of chronologically recording the acquired boundary position along with data of an observation position and the like;

DETAILED DESCRIPTION OF THE PREFERRED EMBODIMENT(S)

Hereinafter, embodiments of the present invention will be described with reference to the drawings.

First Embodiment

Figure 1:
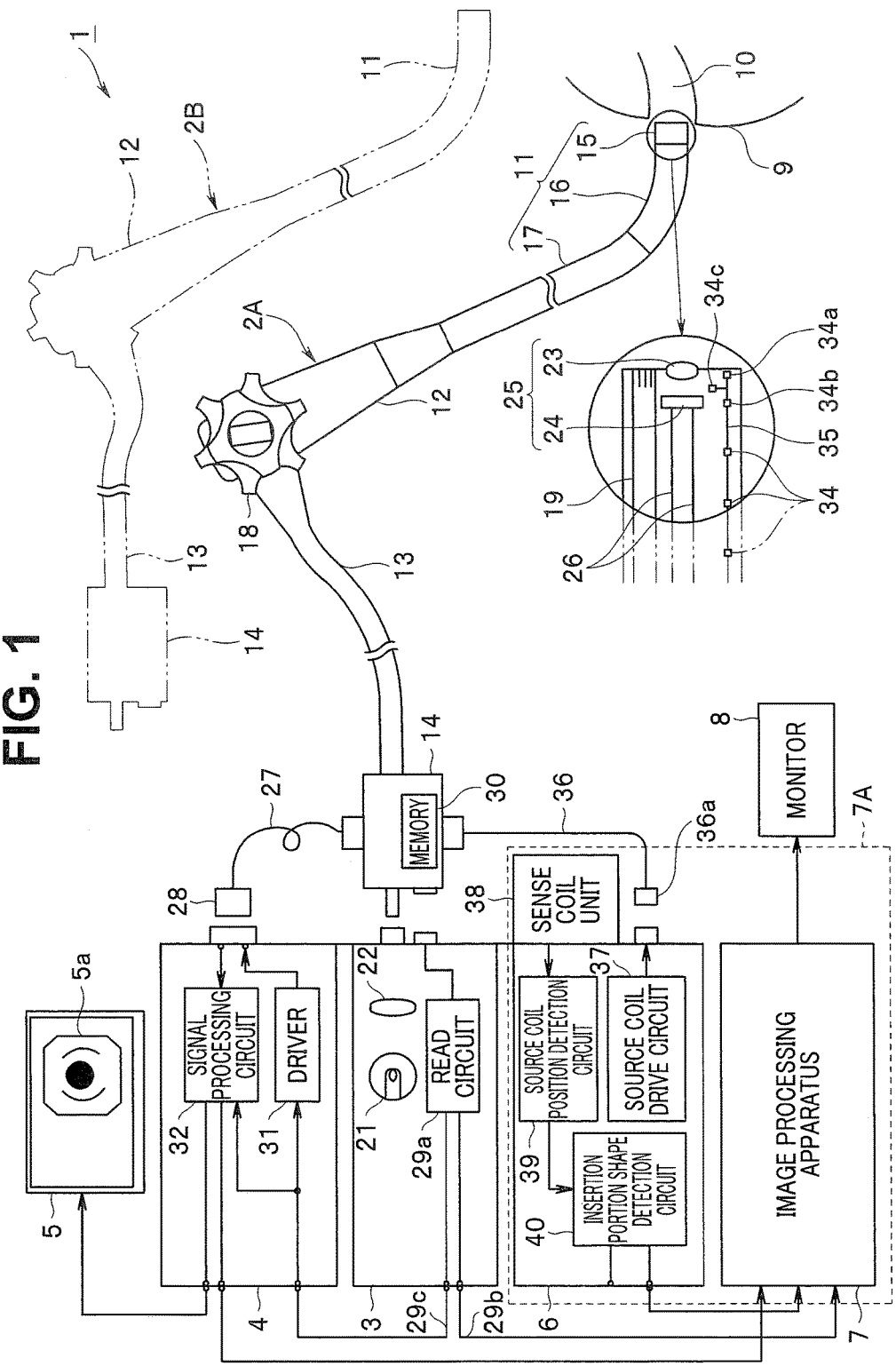
FIG. 1 is a diagram showing an overall configuration of an endoscope system provided with a first embodiment of the present invention.

An endoscope system 1 shown in FIG. 1 includes: an endoscope 2A inserted into a subject; a light source apparatus 3 configured to supply illuminating light to the endoscope 2A; a video processor 4 as a signal processing apparatus configured to apply signal processing to an image pickup section provided on the endoscope 2A; a monitor 5 as an endoscope image display apparatus configured to display an endoscopic image generated by the video processor 4; a UPD apparatus 6 as an insertion portion shape detection apparatus configured to detect an insertion portion shape of the endoscope 2 based on a sensor provided in the endoscope 2A; an image processing apparatus 7 of a first embodiment of the present invention; and a monitor 8 as a display apparatus configured to display an identification image and the like generated by the image processing apparatus 7. Note that in place of the image processing apparatus 7 separate from the UPD apparatus 6 indicated by a solid line in FIG. 1, an image processing apparatus 7A configured to include the UPD apparatus 6 as indicated by a dotted line may be used.

The endoscope 2A includes: an insertion portion 11 inserted into, for example, a urinary tract 10 forming part of a predetermined luminal organ (also simply called a luminal organ) in a subject 9; an operation portion 12 provided on a back end (proximal end) of the insertion portion 11; and a universal cable 13 extended from the operation portion 12. A light guide connector 14 provided on an end portion of the universal cable 13 is detachably connected to a light guide connector receiver of the light source apparatus 3. Note that the urinary tract 10 communicates with a renal pelvis 51a and renal calyces 51b on a deep side of the urinary tract 10 (see FIG. 3).

The insertion portion 11 includes: a distal end portion 15 provided on a distal end of the insertion portion 11; a bendable bending portion 16 provided on a back end of the distal end portion 15; and a flexible tube portion 17 with flexibility extending from a back end of the bending portion 16 to a front end of the operation portion 12.

The operation portion 12 is provided with a bending operation knob 18 for performing bending operation of the bending portion 16.

As shown in a partial enlarged view in FIG. 1, a light guide 19 configured to transmit illuminating light is inserted into the insertion portion 11. A distal end of the light guide 19 is attached to an illuminating window of the distal end portion 15, and a back end of the light guide 19 reaches the light guide connector 14.

Illuminating light generated by a light source lamp 21 of the light source apparatus 3 is condensed by a condensing lens 22, and the illuminating light enters the light guide connector 14. The light guide 19 emits the transmitted illuminating light from a distal end surface attached to the illuminating window.

An optical image of a site to be observed (also called an object) in the luminal organ illuminated by the illuminating light is formed on an image formation position of an objective optical system 23 by the objective optical system 23 attached to an observation window (image pickup window) provided adjacent to the illuminating window of the distal end portion 15. An image pickup surface of, for example, a charge coupled device (abbreviated as CCD) 24 as an image pickup device is arranged at the image formation position of the objective optical system 23. The CCD 24 has a predetermined angle of view (view angle).

The objective optical system 23 and the CCD 24 form an image pickup section (or an image pickup apparatus) 25 configured to pick up an image of an inside of the luminal organ. Note that the angle of view of the CCD 24 also depends on optical characteristics (for example, focal distance) of the objective optical system 23. Therefore, the angle of view of the CCD 24 can also be stated as an angle of view of the image pickup section 25 in which the optical characteristics of the objective optical system 23 are taken into account or as an angle of view of a case of observation using the objective optical system.

The CCD 24 is connected to one end of a signal line 26 inserted into the insertion portion 11 and the like, and the other end of the signal line 26 reaches a signal connector 28 at an end portion of a connection cable 27 through the connection cable 27 (signal line in the connection cable 27) connected to the light guide connector 14. The signal connector 28 is detachably connected to a signal connector receiver of the video processor 4.

The video processor 4 includes: a driver 31 configured to generate a CCD drive signal; and a signal processing circuit 32 configured to apply signal processing to an output signal of the CCD 24 to generate an image signal (video signal) displayed as an endoscopic image on the monitor 5. The driver 31 applies the CCD drive signal to the CCD 24 through the signal line 26 and the like, and as a result of the application of the CCD drive signal, the CCD 24 outputs, as an output signal, an image pickup signal obtained by photoelectrically converting the optical image formed on the image pickup surface.

The image pickup signal outputted from the CCD 24 is converted to an image signal by the signal processing circuit 32, and the signal processing circuit 32 outputs the image signal to the monitor 5 from an output end. The monitor 5 displays an image corresponding to the optical image picked up in a predetermined angle of view (range of the angle of view) formed on the image pickup surface of the CCD 24, as an endoscopic image in an endoscopic image display area (simply abbreviated as an image display area) 5a. FIG. 1 shows a situation of displaying an endoscopic image close to an octagon obtained by cutting out four corners of a square when the image pickup surface of the CCD 24 is square, for example.

The endoscope 2A includes, for example, a memory 30 in the light guide connector 14, the memory 30 storing information specific to the endoscope 2A, and the memory 30 stores angle of view data (or angle of view information) as information indicating the angle of view of the CCD 24 mounted on the endoscope 2A. In the light source apparatus 3, a read circuit 29a provided inside of the light source apparatus 3 reads the angle of view data through an electric contact connected to the memory 30 when the light guide connector 14 is connected to the light source apparatus 3.

The read circuit 29a outputs the read angle of view data to the image processing apparatus 7 through a communication line 29b. The read circuit 29a also outputs the read data of the number of pixels of the CCD 24 to the driver 31 and the signal processing circuit 32 of the video processor 4 through a communication line 29c. The driver 31 generates a CCD drive signal according to the inputted data of the number of pixels, and the signal processing circuit 32 executes signal processing according to the data of the number of pixels.

Note that although the case of providing the read circuit 29a configured to read the information specific to the memory 30 on the light source apparatus 3 is illustrated in the example of configuration shown in FIG. 1, the read circuit 29a may be provided on the video processor 4.

The signal processing circuit 32 outputs, for example, endoscopic image data (also called image data) as a digital image signal to the image processing apparatus 7.

In the insertion portion 11, a plurality of source coils 34 serving as a sensor for detecting an insertion shape when the insertion portion 11 is inserted into the subject 9 are arranged at appropriate intervals in a longitudinal direction of the insertion portion 11. In the distal end portion 15, two source coils 34a and 34b arranged in the longitudinal direction of the insertion portion 11 and a source coil 34c arranged, for example, in a direction orthogonal to a line segment connecting the two source coils 34a and 34b are arranged. A line segment direction connecting the source coils 34a and 34b substantially coincides with an optical axis direction (or visual line direction) of the objective optical system 23 forming the image pickup section 25, and a surface including the three source coils 34a, 34b, and 34c is arranged to substantially coincide with a vertical direction of the image pickup surface of the CCD 24.

Therefore, it can be stated that a source coil position detection circuit 39 described later in the UPD apparatus 6 can detect three-dimensional positions of the three source coils 34a, 34b, and 34c to thereby detect a three-dimensional position of the distal end portion 15 and a longitudinal direction of the distal end portion 15. It can also be stated that the source coil position detection circuit 39 can detect the three-dimensional positions of the three source coils 34a, 34b, and 34c at the distal end portion 15 to thereby detect a three-dimensional position of the objective optical system 23 and the visual line direction (optical axis direction) of the objective optical system 23 forming the image pickup section 25 arranged at already-known respective distances from the three source coils 34a, 34b, and 34c.

The source coil position detection circuit 39 forms an information acquisition section configured to acquire information of the three-dimensional position and the visual line direction of the objective optical system 23.

Note that although the image pickup surface of the CCD 24 is arranged at the image formation position of the objective optical system 23 in the image pickup section 25 of the endoscope 2A shown in FIG. 1, a case of an endoscope including an image pickup section configured to use an image guide configured to transmit the optical image of the objective optical system 23 between the objective optical system 23 and the CCD can also be applied.

The plurality of source coils 34 including the three source coils 34a, 34b, and 34c are connected to one end of a plurality of signal lines 35, and the other end of the plurality signal lines 35 are connected to a cable 36 extended from the light guide connector 14. A signal connector 36a on an end portion of the cable 36 is detachably connected to a signal connector receiver of the UPD apparatus 6.

The UPD apparatus 6 includes: a source coil drive circuit 37 configured to drive the plurality of source coils 34 to generate an alternating magnetic field around each of the source coils 34; a sense coil unit 38 including a plurality of sense coils configured to detect the magnetic field generated by each of the source coils to detect the three-dimensional position of each of the source coils; the source coil position detection circuit 39 configured to detect the three-dimensional position of each of the source coils based on detection signals of the plurality of sense coils; and an insertion shape detection circuit 40 configured to detect the insertion shape of the insertion portion 11 from the three-dimensional position of each of the source coils detected by the source coil position detection circuit 39 to generate an image of the insertion shape.

The three-dimensional position of each of the source coils is detected under a coordinate system of the UPD apparatus 6. On the other hand, a first coordinate system (or CT coordinate system) widely used in a CT (computed tomography) apparatus is used as described later for the image data of the luminal organ into which the insertion portion 11 of the endoscope 2 is inserted. Therefore, three-dimensional position data of a second coordinate system that is the coordinate system of the UPD apparatus 6 is converted to three-dimensional position data of the first coordinate system.

As described, the source coil position detection circuit 39 font's an information acquisition section configured to acquire the information of the observation position (three-dimensional position) and the visual line direction of the objective optical system 23. In a narrower sense, it can also be stated that the source coil position detection circuit 39 and the three source coils 34a, 34b, and 34c form an information acquisition section configured to acquire the information of the observation position and the visual line direction of the objective optical system 23.

Note that the endoscope system 1 (and the image processing apparatus 7) of the present embodiment can also use an endoscope 2B (in place of the endoscope 2A) indicated by an alternate long and two short dashes line in FIG. 1.

The endoscope 2B is an endoscope in which the three source coils 34a, 34b, and 34c are arranged only in the distal end portion 15 of the insertion portion 11 in the endoscope 2A. In the endoscope 2B, the plurality of source coils 34 include the three source coils 34a, 34b, and 34c configured to detect the three-dimensional position (also simply called a position) and the longitudinal direction of the distal end portion 15 of the insertion portion 11, and the other components are the same as the components described in the endoscope 2A (however, specific values, such as the number of pixels and the angle of view of the CCD 24, vary according to the type of the endoscope).

The insertion shape detection circuit 40 includes: a first output end for outputting an image signal of the insertion shape; and a second output end for outputting data of the observation position and the visual line direction (also called position and direction data) of the objective optical system 23 detected by the source coil position detection circuit 39. The data of the observation position and the visual line direction is outputted from the second output end to the image processing apparatus 7. Note that the source coil position detection circuit 39 forming the information acquisition section may output the data of the observation position and the visual line direction outputted from the second output end.

The image processing apparatus 7 mainly uses the data of the observation position and the visual line direction of the objective optical system 23, and a detection apparatus configured to detect the positions of the three source coils 34a, 34b, and 34c arranged on the distal end portion 15 may be used in place of the UPD apparatus 6.

Figure 2:
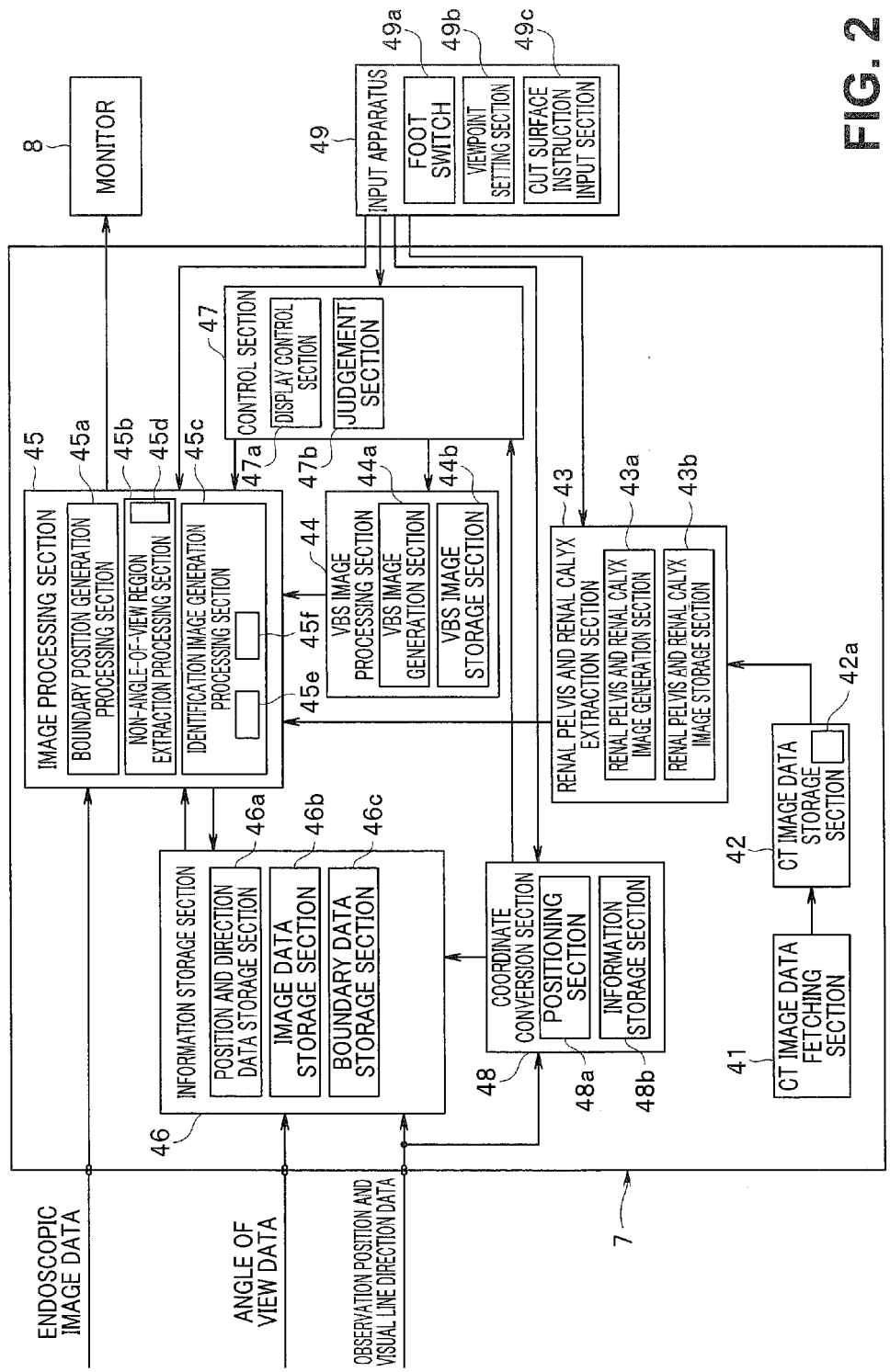
FIG. 2 is a diagram showing a configuration of an image processing apparatus of the first embodiment of the present invention.

FIG. 2 shows a configuration of the image processing apparatus 7 of the first embodiment. The image processing apparatus 7 includes: a CT image data fetching section 41 configured to fetch CT image data as three-dimensional image information of the subject 9 generated by a publicly known CT apparatus through a portable storage medium, such as a DVD, a Blu-ray disc, and a flash memory, for the subject 9 observed and examined by an endoscope 2 (2 represents 2A and 2B); and a CT image data storage section 42 configured to store the CT image data fetched by the CT image data fetching section 41.

Note that the CT image data storage section 42 may store the CT image data of the subject 9 generated by the CT apparatus through a communication line, the Internet, or the like. The CT image data storage section 42 includes a hard disk apparatus, a flash memory, a DVD, or the like.

The CT image data storage section 42 includes a storage section 42a made of a flash memory or the like configured to store the CT image data as three-dimensional image information (or three-dimensional image and position information) associating the CT image data and the three-dimensional position data in the first coordinate system (CT coordinate system) that is a coordinate system indicating each three-dimensional position of the CT image data.

Figure 3:
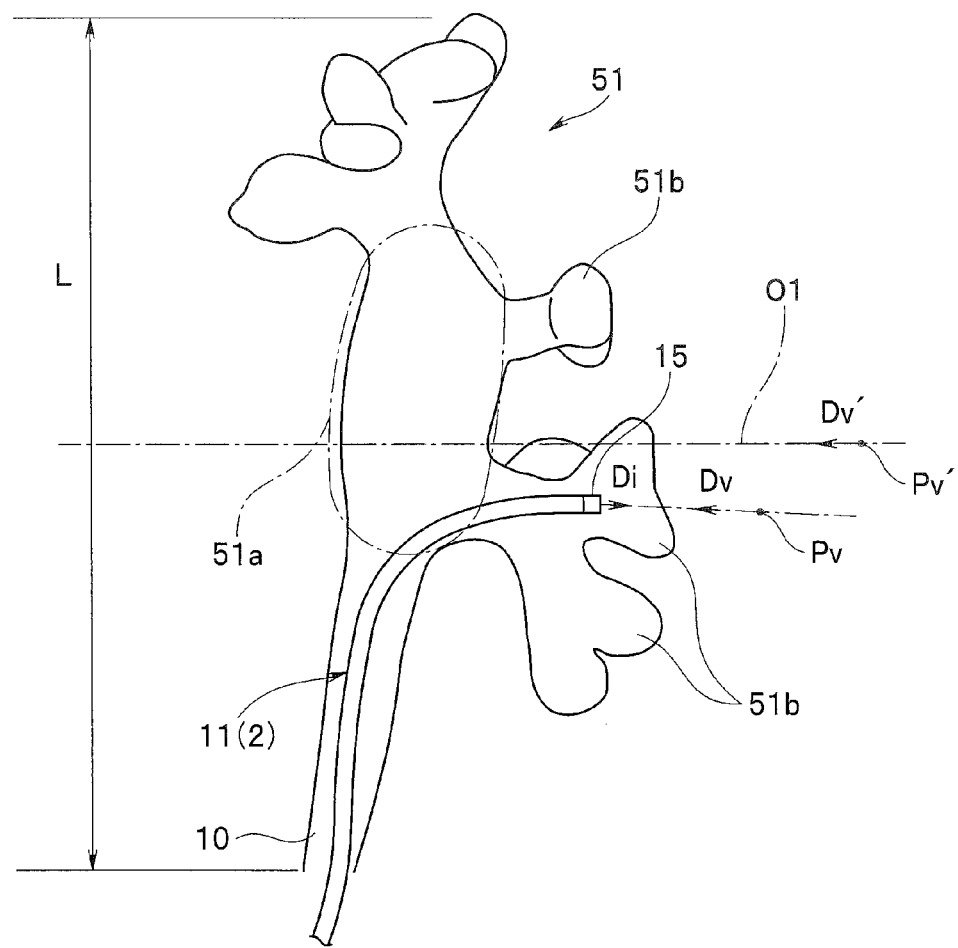
FIG. 3 is an explanatory diagram showing renal pelvis and renal calyces in a state that an insertion portion of an endoscope is inserted.

The image processing apparatus 7 includes a renal pelvis and renal calyx extraction section 43 as a luminal organ extraction section or a luminal organ extraction circuit configured to extract three-dimensional image data of renal pelvis and renal calyces 51 (see FIG. 3) as predetermined luminal organs from the CT image data of the CT image data storage section 42. Note that FIG. 3 shows the renal pelvis and renal calyces 51 in a state that the insertion portion 11 of the endoscope 2 is inserted. In FIG. 3, a region indicated by an alternate long and short dash line is the renal pelvis 51a, and the renal calyces 51b are formed on a deep side of the renal pelvis 51a.

The renal pelvis and renal calyx extraction section 43 generates image information (image data) of three-dimensional shapes indicating hollow shapes of the renal pelvis and renal calyces 51 from the extracted three-dimensional image data (more specifically, three-dimensional volume data) of the renal pelvis and renal calyces 51. That is, the renal pelvis and renal calyx extraction section 43 includes a renal pelvis and renal calyx image generation section 43a made of a renal pelvis and renal calyx image generation circuit configured to generate a renal pelvis and renal calyx shape image in a hollow three-dimensional shape (as a three-dimensional image of predetermined luminal organs) from the extracted three-dimensional image data of the renal pelvis and renal calyces 51. Note that the renal pelvis and renal calyx image generation section 43a can include: an extraction circuit configured to extract the three-dimensional image data of the renal pelvis and renal calyces 51 (see FIG. 3) as the predetermined luminal organs from the CT image data; and a contour extraction circuit configured to extract only an external shape (contour) from the three-dimensional image data of the renal pelvis and renal calyces 51 extracted by the extraction circuit. Note that the CT image data fetching section 41 may fetch the three-dimensional image data of the renal pelvis and renal calyces 51 generated by the CT apparatus or the like or the renal pelvis and renal calyx shape image in the hollow three-dimensional shape.

The renal pelvis and renal calyx image generated by the renal pelvis and renal calyx image generation section 43a is sent to an image processing section (or image processing circuit) 45 described below and is used for image processing by the image processing section 45. Note that the predetermined luminal organs may be defined to include the urinary tract 10 (part of the urinary tract 10) along with the renal pelvis and renal calyces 51.

The renal pelvis and renal calyx image generation section 43a has a function of a display image changing section configured to three-dimensionally generate a three-dimensional image of the renal pelvis and renal calyces 51 as the predetermined luminal organs from an instructed display direction based on, for example, input of an instruction or designation of the display direction from an input apparatus 49. Note that when the instruction or designation of the display direction is inputted from the input apparatus 49, the instruction or designation may be inputted to the renal pelvis and renal calyx image generation section 43a through a control section 47 including a central processing unit (abbreviated as CPU) or the like. The image processing section 45 may have the function of the display image changing section.

The image processing section 45 (identification image generation processing section 45c described later of the image processing section 45) creates an identification image by superimposing identification information (for example, coloring information) on the three-dimensional image of the renal pelvis and renal calyces 51 in which the display direction is changed by the display image changing section. As described later, the image processing section 45 (identification image generation processing section 45c of the image processing section 45) may output, as an identification image, an image with a largest (greatest) proportion of a non-angle-of-view region in the identification image generated by the display image changing section 45e, to the monitor 8 as a display apparatus.

Although FIG. 3 shows the renal pelvis and renal calyces 51 in the state that the insertion portion 11 is inserted in the description above, the three-dimensional (shape) image of the renal pelvis and renal calyces 51 is used in the present embodiment to extract boundary positions, non-angle-of-view regions, and the like as described below. Therefore, although FIGS. 6, 7, and the like illustrated below show images of the renal pelvis and renal calyces 51, the renal pelvis and renal calyces 51 will be indicated by same reference sign 51 for the simplification as in the case of FIG. 3.

When the renal pelvis and renal calyx extraction section 43 extracts the image data of the three-dimensional shape of the renal pelvis and renal calyces 51, the renal pelvis and renal calyx extraction section 43 extracts the image data in association with three-dimensional position data in the first coordinate system corresponding to the image data. The renal pelvis and renal calyx extraction section 43 includes a renal pelvis and renal calyx image storage section 43b including a memory or the like configured to store the information associating the image data of the three-dimensional shape of the renal pelvis and renal calyces 51 (that is, renal pelvis and renal calyx shape image data) with the three-dimensional position data. The renal pelvis and renal calyx image storage section 43b may be stored in an information storage section 46 described later.

The image processing apparatus 7 includes a VBS image processing section 44 configured to generate a virtual endoscopic image (will be called a VBS image) of a case in which an image is picked up by virtually arranging the image pickup section 25 provided on the distal end portion 15 at a desired position in the renal pelvis and renal calyces 51 and virtually setting the visual line direction.

The VBS image processing section 44 includes: a VBS image generation section 44a including a VBS image generation circuit configured to generate a VBS image; and a VBS image storage section 44b including a memory or the like configured to store the generated VBS image. Note that the VBS image storage section 44b may be provided outside of the VBS image processing section 44.

The image processing apparatus 7 includes the image processing section (or image processing circuit) 45 configured to execute image processing of a boundary position generation processing section 45a and the like forming a boundary position generation section configured to generate data (information) of a boundary position that is a boundary between an angle-of-view region obtained by actually picking up an image by the image pickup section 25 having a predetermined angle of view and a non-angle-of-view region that is outside of the angle of view and not photographed, on the three-dimensional image (three-dimensional shape image) of the renal pelvis and renal calyces, after the input of the endoscopic image data or the like as image data of a case that an image of the inside of the renal pelvis and renal calyces as luminal organs is picked up. The image processing section 45 may be formed like software by using a CPU or may be formed by using hardware such as a dedicated electronic circuit. Note that the boundary position generation processing section (or boundary position generation processing circuit) 45a, a non-angle-of-view region extraction processing section (or non-angle-of-view region extraction processing circuit) 45b, the identification image generation processing section (or identification image generation processing circuit) 45c, and the like in the image processing section 45 may be similarly formed like software by using CPUs or may be formed by using hardware such as dedicated electronic circuits. The renal pelvis and renal calyx extraction section 43, the VBS image processing section 44, the control section 47, and a coordinate conversion section 48 shown in FIG. 2 may also be formed by CPUs or may be formed by using hardware such as dedicated electronic circuits.

In the boundary position (data of boundary position) generated by the boundary position generation processing section 45a, the observation position and the visual line direction of the objective optical system 23 chronologically changes due to movement of the distal end portion 15 of the insertion portion 11.

The non-angle-of-view region extraction processing section 45b provided in the image processing section 45 has a function of a non-angle-of-view region extraction section configured to execute a process of extracting a non-angle-of-view region not in the angle of view of the image pickup section 25 in the three-dimensional image of the renal pelvis and renal calyces 51 as luminal organs based on the data of the boundary position that changes along with the temporal change in the observation position and the visual line direction of the objective optical system 23. The image processing section 45 (for example, the non-angle-of-view region extraction processing section 45b of the image processing section 45) includes an angle-of-view region extraction processing section (or an angle-of-view region extraction processing circuit) 45d as an angle-of-view region extraction section configured to execute a process of extracting an angle-of-view region within the angle of view of the image pickup section 25 in the three-dimensional image of the renal pelvis and renal calyces 51 as luminal organs based on the data of the boundary position that changes along with the temporal change in the observation position and the visual line direction of the objective optical system 23. As described, since the angle-of-view region is a region within the angle of view of the image pickup section 25, the angle-of-view region is a region including a boundary position that chronologically changes. In other words, the angle-of-view region extraction processing section 45d executes a process of extracting a set of boundary positions acquired in the past as an angle-of-view region or a process of including the set in the angle-of-view region.

The image processing section 45 includes the identification image generation processing section (or identification image generation processing circuit) 45c forming an identification image generation section configured to generate an identification image including superimposed identification information for distinguishing the non-angle-of-view region extracted by the non-angle-of-view region extraction processing section 45b on the renal pelvis and renal calyx image generated by the renal pelvis and renal calyx image generation section 43a from the angle-of-view region. For the identification information for distinguishing the non-angle-of-view region from the angle-of-view region on the renal pelvis and renal calyx image, the identification image generation processing section 45c colors and displays the non-angle-of-view region side, for example (see FIG. 7).

The image processing apparatus 7 includes an information storage section 46 including a memory and the like configured to store a position and direction data storage section 46a and the like configured to store the data of the observation position and the visual line direction of the objective optical system 23 inputted from the UPD apparatus 6.

Note that the position and direction data storage section 46a may store the data of the observation position and the visual line direction of the objective optical system 23 after conversion to the first coordinate system (from the second coordinate system) by the coordinate conversion section 48 described later or may store the data of the observation position and the visual line direction of the objective optical system 23 in both coordinate systems before the conversion and after the conversion. In operation described later, a case of storing the data of the observation position and the visual line direction in the first coordinate system after the conversion will be described.

The information storage section 46 also includes: an angle-of-view data storage section 46b configured to store the angle of view data (of the image pickup section 25) inputted from the read circuit 29a; and a boundary data storage section 46c configured to store the data of the boundary position generated by the boundary position generation processing section 45a of the image processing section 45. The boundary data storage section 46c, for example, chronologically (in order of time period) stores the data of the boundary positions generated by the boundary position generation processing section 45a along with data of the time. The non-angle-of-view region extraction processing section 45b uses the data of the chronologically generated boundary positions and the three-dimensional image data of the renal pelvis and renal calyces 51 to execute the process of extracting the non-angle-of-view region.

The image processing apparatus 7 includes: the control section 47 configured to control the operation of the image processing section 45, the information storage section 46, and the like inside of the image processing apparatus 7; and the coordinate conversion section (or coordinate conversion circuit) 48 configured to convert the data of the distal end portion 15 (or observation position of the objective optical system 23 provided on the distal end portion 15) in the second coordinate system acquired (detected) in the luminal organ by the information acquisition section (formed by the source coil position detection circuit 39 in the UPD apparatus 6) to the data of the three-dimensional position of the first coordinate system as a coordinate system indicating the three-dimensional position in the three-dimensional image of the luminal organ.

Figure 7:
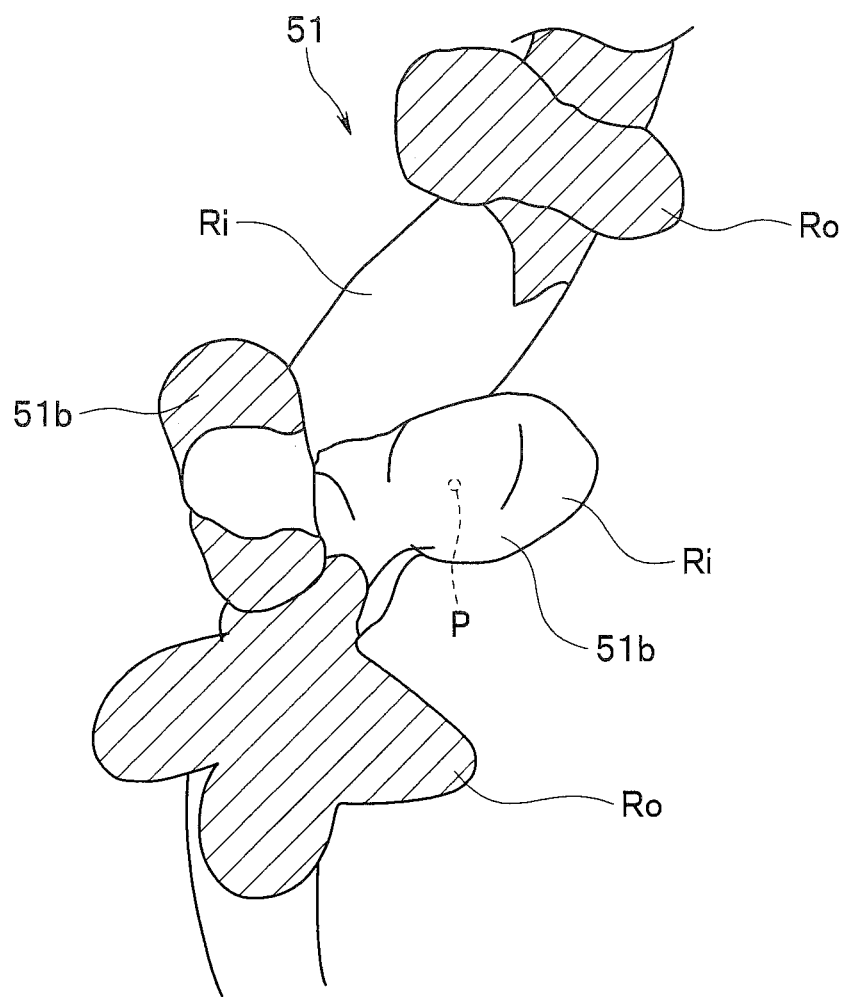
FIG. 7 is a diagram showing a situation of distinguishing and displaying angle-of-view regions and non-angle-of-view regions picked up in the angle of view of the image pickup section.

The control section 47 has a function of a display control section (or display control circuit) 47a configured to control ON/OFF of the display of the identification image for distinguishing the non-angle-of-view region from the angle-of-view region generated by the identification image generation processing section (or identification image generation processing circuit) 45c of the image processing section 45. For example, when the surgeon gives an instruction of display ON from the input apparatus 49 to display the identification image, the display control section 47a performs control to display and distinguish the non-angle-of-view region from the angle-of-view region in the identification image generated by the identification image generation processing section 45c (FIG. 7 described later). On the other hand, when the surgeon gives an instruction of display OFF for turning off the display of the identification image, the display control section 47a performs control to display the non-angle-of-view region without distinguishing the non-angle-of-view region from the angle-of-view region in the identification image generated by the identification image generation processing section 45c (coloring as identification information indicated by oblique lines in FIG. 7 is stopped). Note that the input apparatus 49 (for example, a foot switch 49a of the input apparatus 49) has a function of a display switch section for selectively turning on and off the display of the identification image.

The control section 47 has a function of a judgement section (or judgement circuit) 47b including a comparison circuit or the like configured to judge whether the chronological movement of the objective optical system 23 by the information acquisition section and the image in the predetermined luminal organ acquired by the image pickup section 25 by using the objective optical system 23 satisfy predetermined conditions.

The predetermined conditions are conditions as follows.

a) Moving distance that a distance between the observation position of a previous time and the observation position of a current time of the objective optical system 23 acquired by the information acquisition section is equal to or smaller than a threshold.

b) Movement (or movement direction) reversal that the movement direction of the objective optical system 23 acquired by the information acquisition section is reversed.

c) Pixel values that a sum of luminance values of at least a plurality of pixels included in the object image acquired by the image pickup section 25 is equal to or greater than a threshold.

d) Near distance that a distance from the current observation position of the objective optical system 23 acquired by the information acquisition section to the three-dimensional shape of the renal pelvis and renal calyces in the visual line direction from the position is equal to or smaller than a threshold. The predetermined conditions include one of the conditions or two or more of the conditions. Note that the observation position and the movement direction of the objective optical system 23 after the coordinate conversion by the coordinate conversion section 48 may be used as the observation position and the movement direction of the objective optical system 23 acquired by the information acquisition section in the judgement of the predetermined conditions.

The judgement section 47b of the control section 47 temporally monitors the data of the observation position of the objective optical system 23 through, for example, the coordinate conversion section 48 and judges whether the conditions a), b), and d) are satisfied. The judgement section 47b of the control section 47 temporally monitors the endoscopic image data to judge whether the condition c) is satisfied. The process corresponding to the predetermined conditions is FIG. 5B. In other words, when the inner surface of the luminal organ is observed in the present embodiment, the angle-of-view region and the non-angle-of-view region are basically extracted only from the data of the boundary position of the angle of view in a normal observation state not corresponding to the conditions, and the non-angle-of-view region that is not observed can be identified by a small amount of calculation.

The coordinate conversion section 48 includes a positioning section (or positioning processing circuit) 48a configured to align, at already-known three-dimensional positions, the three-dimensional position data of the observation position of the objective optical system 23 in the second coordinate system acquired by the information acquisition section with the three-dimensional position data of the first coordinate system as a coordinate system used to acquire the three-dimensional image of the luminal organ.

Figure 4:
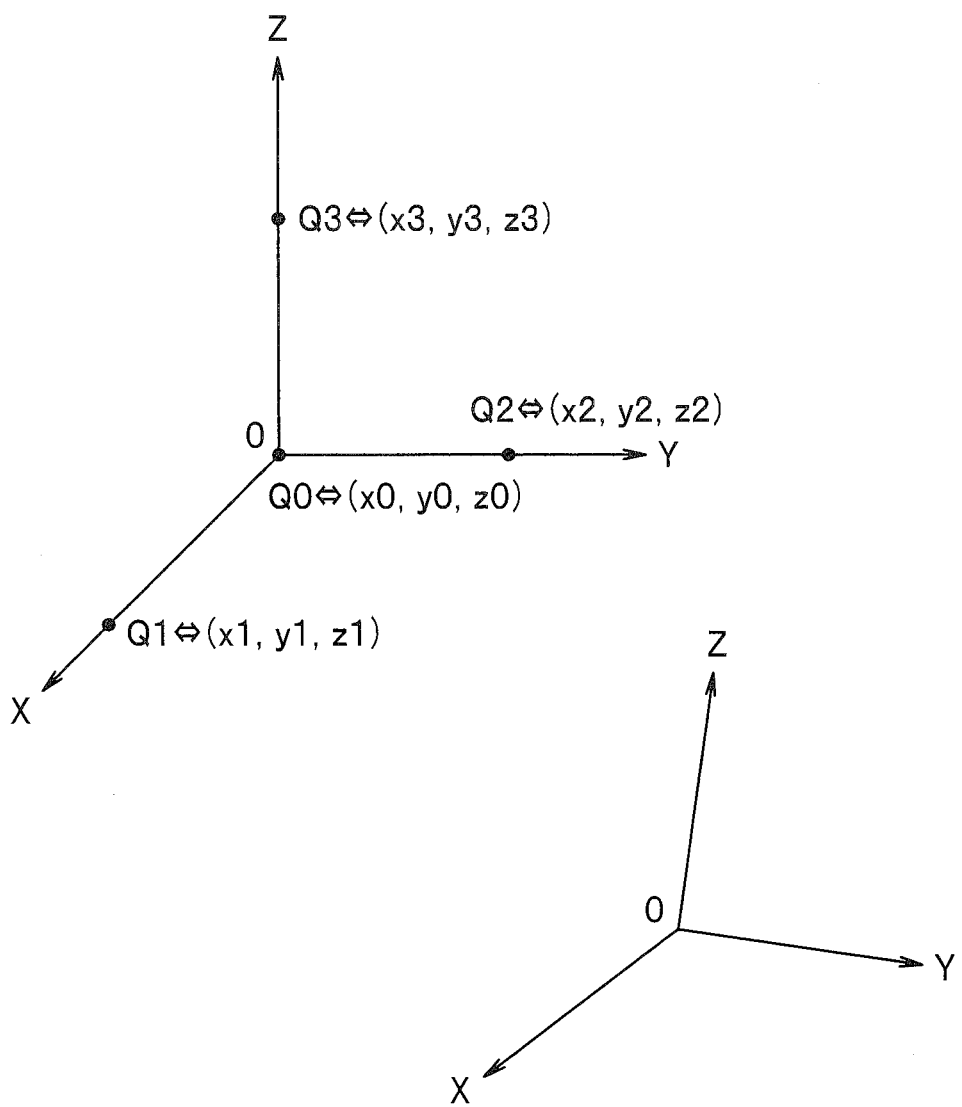
FIG. 4 is an explanatory diagram of a case of positioning (associating) same positions in two coordinate systems.

The positioning section 48a performs the alignment as shown in FIG. 4 at a plurality of already-known positions (for example, four parts Q0 to Q3) near the insertion port of the urinary tract 10 as shown in FIG. 1, for example.

The position alignment is instructed from, for example, the input apparatus 49 in each of the first coordinate system O-XYZ and the second coordinate system o-xyz. The position alignment in this case is performed for a plurality of already-known positions in both coordinate systems as described below.

For example, the distal end portion 15 is sequentially set to a position Q0 (0, 0, 0) of an origin O, a position Q1 (1, 0, 0) on an X coordinate, a position Q2 (0, 1, 0) on a Y coordinate, and a position Q3 (0, 0, 1) on a Z coordinate in the first coordinate system O-XYZ, and the surgeon instructs the position alignment. Assuming that the positions sequentially acquired by the information acquisition section at each position in the instruction are (x0, y0, z0), (x1, y1, z1), (x2, y2, z2), and (x3, y3, z3), the positioning section 48a performs the positioning and stores the information of positioning in an information storage section 48b or the like in the coordinate conversion section 48.

The information storage section 48b stores the positioning information in this case (more specifically, (x0, y0, z0), (x1, y1, z1), (x2, y2, z2), and (x3, y3, z3) in the second coordinate system o-xyz are information corresponding to Q0 (0, 0, 0), Q1 (1, 0, 0), Q2 (0, 1, 0), and Q3 (0, 0, 1) in the first coordinate system O-XYZ, respectively). Note that since three source coils 34a, 34b, and 34c are arranged in the distal end portion 15, a similar process is repeated for each source coil, and positioning information with sufficiently small errors can be used.

The coordinate conversion section 48 uses the positioning information stored in the information storage section 48b to determine conversion information for associating arbitrary positions of both coordinate systems. The information storage section 48b also stores the conversion information. The coordinate conversion section 48 uses the conversion information to convert the position data of the observation position and the like of the objective optical system 23 of the second coordinate system to the position data of the first coordinate system.

In FIG. 4, the coordinate positions Q0 (0, 0, 0), Q1 (1, 0, 0), Q2 (0, 1, 0), and Q3 (0, 0, 1) and the respective corresponding coordinate positions (x0, y0, z0), (x1, y1, z1), (x2, y2, z2), and (x3, y3, z3) are simplified and indicated as Q0 ↔ (x0, y0, z0), Q1 ↔ (x1, y1, z1), Q2 ↔ (x2, y2, z2), and Q3 ↔ (x3, y3, z3).

Note that after first positioning, the insertion portion 11 may be inserted toward the renal pelvis and renal calyces 51 on the deep side of the urinary tract 10, and the positioning may be instructed from the input apparatus 49 at a position (for example, at a branched boundary position) that allows easily performing the positioning on the image of the renal pelvis and renal calyces 51 to perform the alignment again.

The input apparatus 49 includes a keyboard, a mouse, and the like, and a user, such as a surgeon, can input operation parameters, data of initial setting, instructions, and the like from the input apparatus 49 to the image processing section 45 and the control section 47 of the image processing apparatus 7 and to the positioning section 48a of the coordinate conversion section 48.

The foot switch 49a is provided on the input apparatus 49, and a first mode for displaying the identification image by the image processing section 45 and a second mode for not displaying the identification image can be selectively switched by ON/OFF operation using the foot switch 49a. The foot switch 49a forms a display switch section capable of switching between the first mode and the second mode. Note that the display switch section may be able to switch between the first mode and the second mode by operation of a scope switch provided on the operation portion 12 of the endoscope 2A or the like along with the foot switch 49a or in place of the foot switch 49a.

The image processing apparatus 7 with the configuration includes: the CT image data storage section 42 forming a storage section configured to store information of a three-dimensional image of the subject 9 acquired in advance; the renal pelvis and renal calyx extraction section 43 forming a luminal organ extraction section configured to extract renal pelvis and renal calyces as predetermined luminal organs existing in the three-dimensional image; the source coil position detection circuit 39 forming an information acquisition section configured to acquire information of an observation position and a visual line direction for observing an inside of the predetermined luminal organs by using the objective optical system 23; the boundary position generation processing section 45a forming a boundary position generation section configured to generate boundary position information indicating a boundary position of an angle-of-view region and a non-angle-of-view region on the three-dimensional image of the predetermined luminal organs based on the information of the observation position and the visual line direction and based on angle of view information indicating an angle of view in a case of observation using the objective optical system 23; the non-angle-of-view region extraction processing section 45b forming a non-angle-of-view region extraction section configured to extract the non-angle-of-view region not in the angle of view in the three-dimensional image of the predetermined luminal organs based on the boundary position information that changes with a temporal change in the observation position and the visual line direction; and the identification image generation processing section 45c forming an image generation section configured to generate an identification image in which identification information for identifying the non-angle-of-view region is added or superimposed on the three-dimensional image of the predetermined luminal organs.

Next, operation of the present embodiment will be described. The endoscope 2A or 2B (represented by 2) shown in FIG. 1 is connected to the light source apparatus 3 or the like, and power of each apparatus is turned on to set the endoscope system 1 including the image processing apparatus 7 to an operation state. In first step S1, the read circuit 29a of the light source apparatus 3 reads the angle of view data of the image pickup section 25 of the connected endoscope 2 from the memory 30 and sends the read angle of view data to the image processing apparatus 7. The image processing apparatus 7 stores the acquired angle of view data in the angle-of-view data storage section 46b. The angle of view data is used by the VBS image generation section 44a.

In next step S2, the surgeon gives an instruction of position alignment from the input apparatus 49, and the positioning section 50a performs positioning for aligning, with the first coordinate system, the data of the three-dimensional positions of the three source coils 34a, 34b, and 34c in the distal end portion 15 acquired (detected) in the second coordinate system by the source coil position detection circuit 39 forming the information acquisition section. Then, the conversion information is determined. Subsequently, the acquired data of the observation position and the visual line direction of the objective optical system 23 is converted to the data of the observation position and the visual line direction in the first coordinate system by coordination conversion by the coordinate conversion section 48 using the conversion information.

In next step S3, the surgeon inserts the insertion portion 11 into the renal pelvis and renal calyces 51 on the deep side of the urinary tract 10.

In next step S4, the source coil position detection circuit 39 sequentially acquires the data of the observation position and the visual line direction of the objective optical system 23 at predetermined time intervals or the like, and the coordinate conversion section 48 converts the coordinates. The position and direction data storage section 46a of the information storage section 46 stores the converted data of the observation position and the visual line direction of the objective optical system 23.

The source coil position detection circuit 39 acquires the data of the observation position and the visual line direction of the objective optical system 23. In the state that the coordinates are converted, the VBS image generation section 44a uses the converted data of the observation position and the visual line direction of the objective optical system 23 and the angle of view data stored in the angle-of-view data storage section 46b to generate the VBS image corresponding to the endoscopic image actually picked up by the image pickup section 25 as shown in step S5.

That is, the VBS image generation section 44a generates a VBS image in the case of observing the inside of the renal pelvis and renal calyces by a virtualized endoscope by using the acquired angle of view based on the converted observation position and visual line direction of the objective optical system 23 on the renal pelvis and renal calyx (shape)

image generated by the renal pelvis and renal calyx image generation section 43*a*. The generated VBS image is outputted to the boundary position generation processing section 45*a* of the image processing section 45. Pattern matching of the endoscopic image actually picked up by the image pickup section 25 and the VBS image generated by the VBS image generation section 44*a* may be performed in step S5, and the VBS image of a case satisfying a matching condition equal to or greater than a preset threshold may be used.

Figures 6A, 6B:
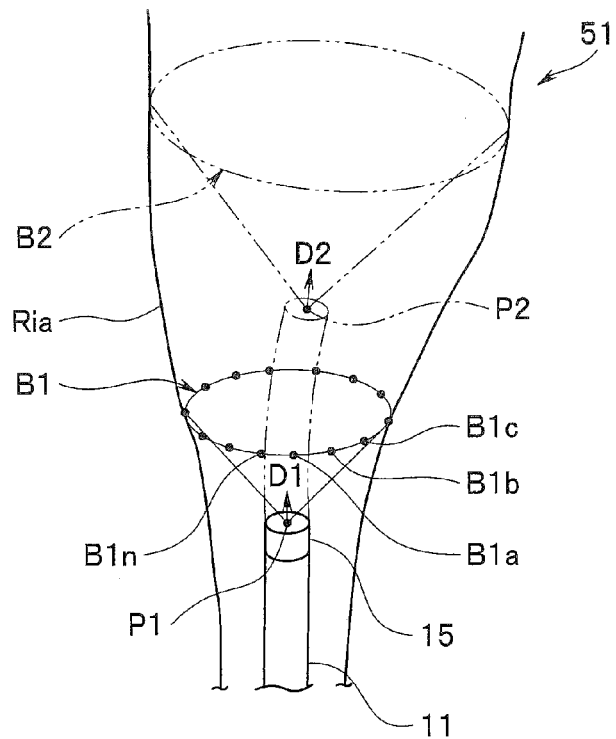

As shown in step S6, the boundary position generation processing section 45*a* acquires (extracts) the data (information) of the boundary position that is a boundary of the angle of view in the generated VBS image from the image (shape) of the renal pelvis and renal calyces 51. FIG. 6A shows surroundings of a boundary position B1 acquired at a time t1, wherein P1 is a position of the distal end portion 15 (observation position of the objective optical system 23 of the distal end portion 15). FIG. 6A shows a case near an entrance from the urinary tract 10 to the renal pelvis 51*a*. The boundary position B1 acquired first is set to a position without a region outside of the angle of view. In the example of FIG. 6A, the boundary position B1 as a position where a conical line (end portion of the conical line) indicating the boundary of the angle of view touches the inner surface of the renal pelvis and renal calyces 51 has a boundary shape close to a circle or an ellipse that can be approximated by positions B1*a*, B1*b*, B1*c*, . . . , and B1*n*.

Note that since the boundary position corresponding to the boundary of the angle of view is acquired in acquiring the data of the boundary position, only part of the VBS image near the boundary of the angle of view may be generated. The data of the boundary position may be acquired (extracted) from the image (shape) of the renal pelvis and renal calyces 51 by using the information of the boundary of the angle of view (conical line in FIG. 6A) based on the observation position and the visual line direction of the objective optical system 23 as shown for example in FIG. 6A without generating the VBS image.

The boundary position generation processing section 45*a* notifies the control section 47 of the acquisition of the data of the boundary position B1, and the control section 47 controls the information storage section 46 to store the data of the boundary position B1. As shown in step S7, the boundary data storage section 46*c* of the information storage section 46 stores the data of the boundary position B1 acquired at the observation position P1 and in a visual line direction D1, along with the data of the time t1. FIG. 6B shows the boundary position B1 and the time t1 stored in the boundary data storage section 46*c*. The boundary position B1 actually indicates the plurality of positions B1*a*, B1*b*, B1*c*, . . . , Bn expressed by the first coordinate system. Note that FIG. 6B also shows a case of a boundary position B2 acquired at an observation position P2 and in a visual line direction D2 (described later), in a time t2 after the time t1.

As shown in step S8, the control section 47 (or the boundary data storage section 46*c*) judges whether the data of the boundary position is already stored in the past. A case this time is a case in which the data of the boundary position B1 is stored first, and in this case, the process moves to step S13.

On the other hand, if the data of the boundary position is stored in the past, a suggestion for setting a viewpoint position and a direction (viewpoint direction) for display is displayed in next step S9. The surgeon inputs data for designating the viewpoint position and direction for display, from the input apparatus 49 to the non-angle-of-view region extraction processing section 45*b* of the image processing section 45, to set the viewpoint position and direction. An example of setting the viewpoint position and direction for display will be described in the renal pelvis and renal calyces 51 shown in FIG. 3.

The visual line direction of the distal end portion 15 (the objective optical system 23 mounted on the distal end portion 15) of the insertion portion 11 of the endoscope 2 inserted into the renal pelvis and renal calyces 51 is on a visual line direction Di of the objective optical system 23, and a viewpoint position Pv is set at a position outside of the renal pelvis and renal calyces 51 (by designation from the input apparatus 49). A direction of viewing the renal pelvis and renal calyces 51 side (opposite the visual line direction Di) at the viewpoint position Pv is a viewpoint direction Dv.

Note that in the description above, the viewpoint position Pv for display is a position on the visual line direction Di of the objective optical system 23 in the distal end portion 15 of the insertion portion 11, and the viewpoint direction Dv is a direction opposite the visual line direction Di. The viewpoint position Pv and the viewpoint direction Dv change in conjunction with the movement of the distal end portion 15.

On the other hand, the viewpoint position Pv and the viewpoint direction Dv for display may not be in conjunction with the movement of the distal end portion 15. For example, a viewpoint direction Dv' of a case not in conjunction with the movement of the distal end portion 15 may be set to a direction of viewing the renal pelvis and renal calyces 51 side along a center line O1 of a range L in a vertical direction of the renal pelvis and renal calyces 51 shown in FIG. 3, and a viewpoint position Pv' of the case not in conjunction may be set on the center line O1.

Note that the user, such as a surgeon, may be able to freely or selectively set the viewpoint position Pv on the visual line direction D1 and the viewpoint position Pv' on the center line O1.

In next step S10, the non-angle-of-view region extraction processing section 45*b* uses the past data of the boundary position chronologically stored in the boundary data storage section 46*c* to extract the non-angle-of-view region (data of the non-angle-of-view region) from the renal pelvis and renal calyx (shape) image. A set of the past data of the boundary position is also extracted as an angle-of-view region from the renal pelvis and renal calyx (shape) image.

In next step S11, the identification image generation processing section 45*c* generates an identification image superimposing the identification information to allow distinguishing the non-angle-of-view region from the angle-of-view region extracted in step S10 on the renal pelvis and renal calyx (shape) image viewed from the viewpoint position and direction set in step S9. In the present embodiment, the identification information is coloring information that allows distinguishing the non-angle-of-view region from the angle-of-view region by color. Note that the user may be able to select and set a color, such as blue, from a plurality of colors when the identification information is colored.

In next step S12, the monitor 8 displays the identification image. More specifically, the monitor 8 displays, as an identification image, the image (shape) of the renal pelvis and renal calyces 51 (as viewed from the viewpoint position and direction set in step S9) in the state that the non-angle-of-view region is colored (in other words, in the state that the identification information is superimposed on the non-angle-of-view region). FIG. 7 shows an identification image three-dimensionally displayed on the monitor 8 when the distal end portion 15 of the insertion portion 11 is inserted into the position shown in FIG. 3.

That is, FIG. 7 displays an identification image in a state that regions indicated by oblique lines are non-angle-of-view regions Ro and can be distinguished from angle-of-view regions Ri not indicated by oblique lines when the image (shape) of the renal pelvis and renal calyces 51 is viewed in the viewpoint direction Dv at the viewpoint position Pv in FIG. 3. In FIG. 3, the distal end portion 15 of the insertion portion 11 is inserted into one of the renal calyces 51b in a direction of the plane of paper of FIG. 3, and the distal end portion 51 is not inserted toward the other renal calyx 51b on an upper side in a perpendicular direction of the plane of paper. Therefore, regions of the other renal calyx 51b side excluding a central side are non-angle-of-view regions Ro as shown in FIG. 7. Note that the angle-of-view regions Ri and the non-angle-of-view regions Ro shown in FIG. 7 are angle-of-view regions and non-angle-of-view regions finally determined through a process in a case that predetermined conditions in FIG. 5B (described later) are satisfied, among the regions extracted only from the data of the boundary position.

Although the non-angle-of-view region Ro side is colored in the identification information that allows distinguishing the angle-of-view regions Ri and the non-angle-of-view regions Ro in the example described in FIG. 7, image parts of the angle-of-view regions Ri may be deleted or may be transparent, for example. Only images of the non-angle-of-view regions Ro as unobserved (or unexamined) regions may be displayed without displaying the images of the angle-of-view regions Ri. Note that as indicated by a dotted line in FIG. 7, an observation position P of the objective optical system 23 (or the position of the distal end portion 15) corresponding to the identification image of FIG. 7 may be superimposed and displayed. A plurality of observation positions of the objective optical system 23 before obtaining the identification image of FIG. 7 may also be superimposed and displayed.

When a three-dimensional shape is expressed by a polygon in generating a renal pelvis and renal calyx shape image in a hollow three-dimensional shape from the extracted three-dimensional image data of the renal pelvis and renal calyces 51, the color of the polygon judged as a non-angle-of-view region may be changed to a color different from the angle-of-view region in the process of step S11 to generate an identification image, and the identification image may be displayed on the monitor 8 in the process of step S12.

Figure 5A:
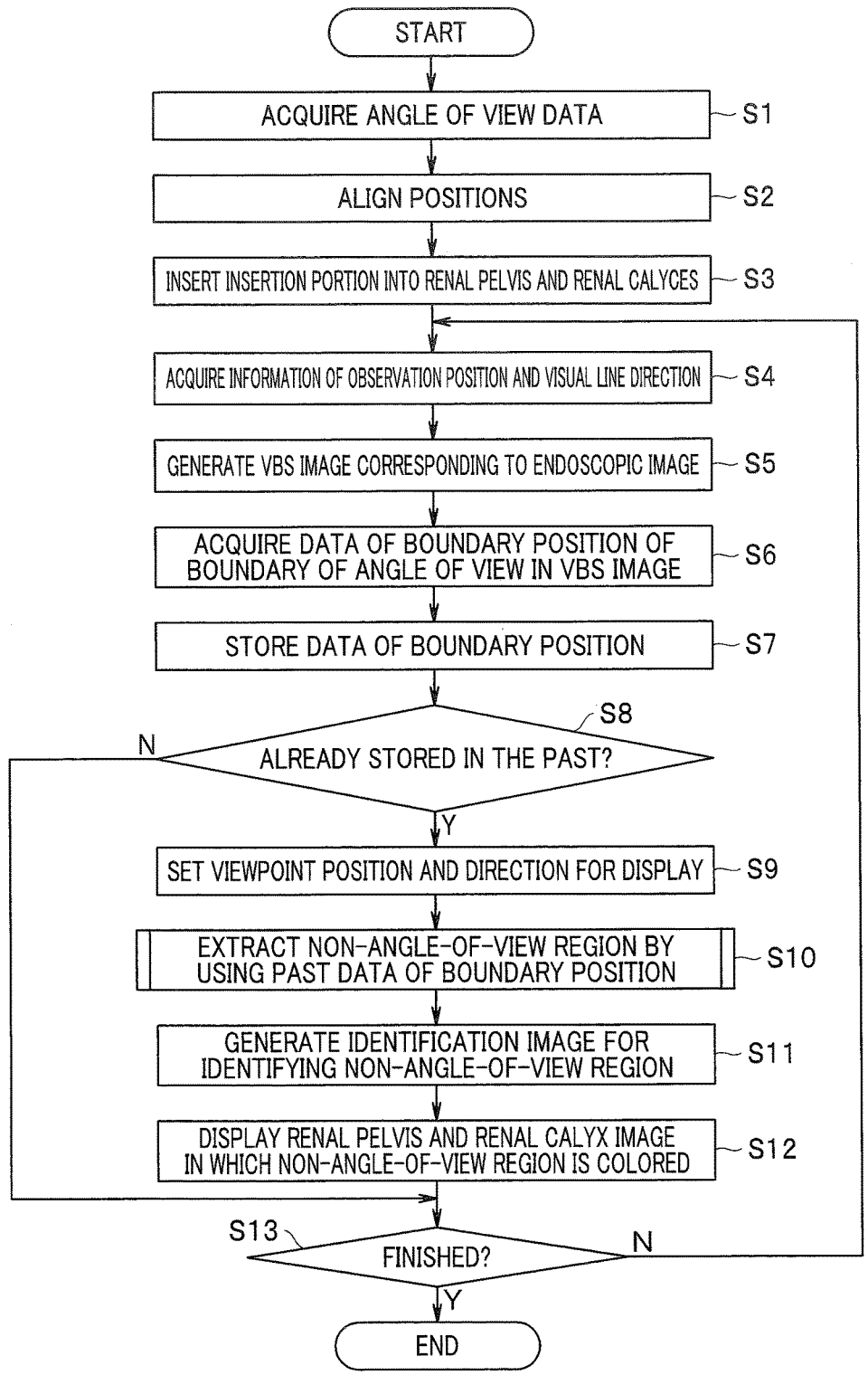
FIG. 5A is a flow chart showing a processing example including a process of the first embodiment of the present invention.

In next step S13, the control section 47 judges whether an instruction for ending the examination is inputted from the input apparatus 49 and ends the process of FIG. 5A if an instruction for ending the examination is inputted. On the other hand, if an instruction for ending the examination is not inputted, the process returns to step S4, and assuming that the process described above is a first process, a second process is executed.

In FIG. 6A, an alternate long and two short dashes line shows the boundary position B2 acquired at the observation position P2 and in the time t2 in the second process. A luminal inner surface in the middle of the boundary positions B1 and B2 is a region where the boundary of the angle of view goes through and is an angle-of-view region Ria.

After the second process, a third process, a fourth process, . . . are repeated until an instruction for ending the examination is provided. In this way, the non-angle-of-view region extraction processing section 45b executes the process of extracting the non-angle-of-view regions between an initial position and an end position (or a final position) in a state that the observation is finished, wherein the initial position is the observation position of the objective optical system 23 in the initial state. The non-angle-of-view region extraction processing section 45b also executes the process of extracting the angle-of-view regions between the initial position and the end position in the state that the observation is finished.

Figure 5B:
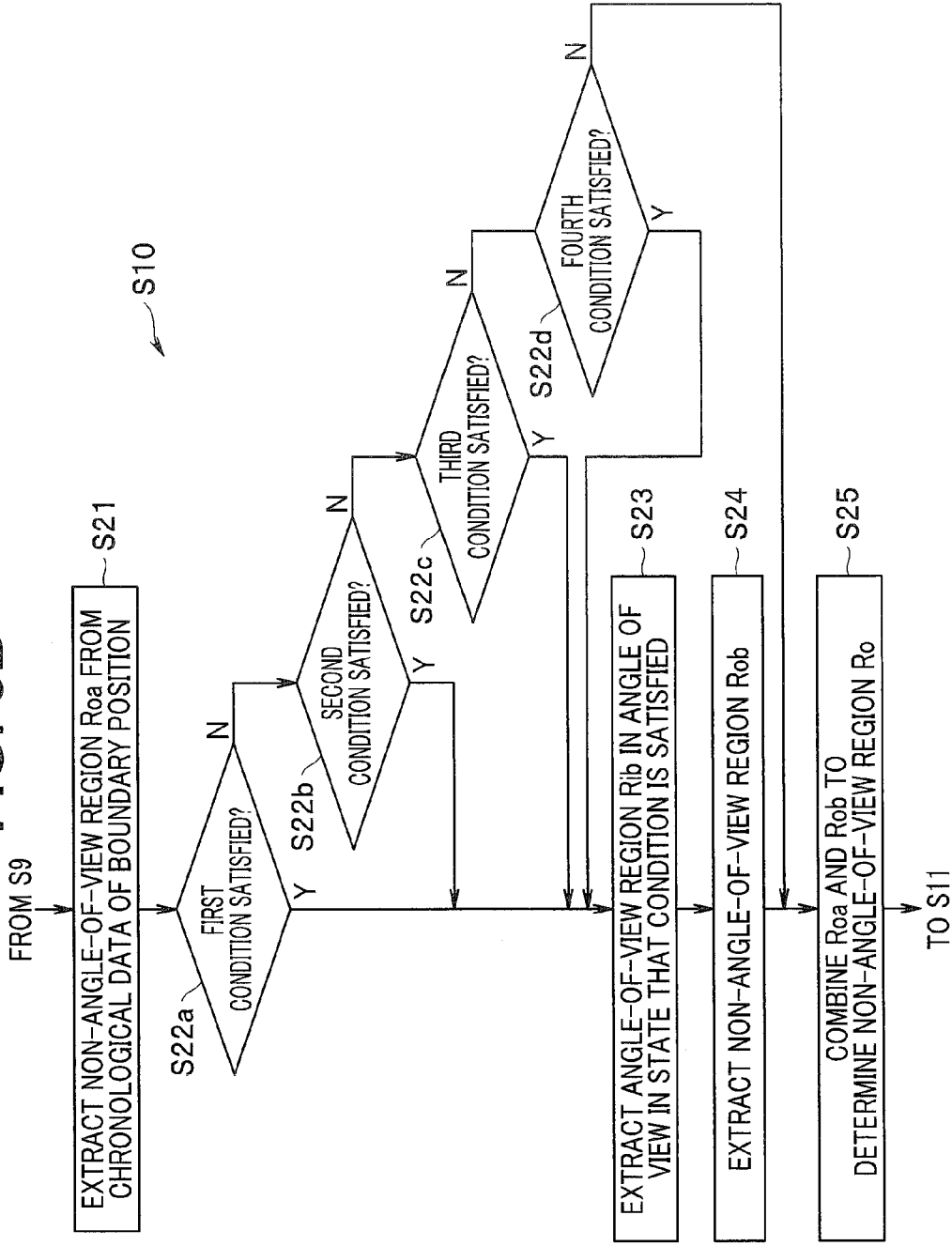
FIG. 5B is a flowchart showing a detailed process of step S10 in FIG. 5A.

For the process of step S10 in FIG. 5A, judgement of whether predetermined conditions are satisfied may be included in addition to the past boundary position data as shown in FIG. 5B to execute the process of extracting the non-angle-of-view regions.

As shown in step S21 of FIG. 5B, the non-angle-of-view region extraction processing section 45b extracts non-angle-of-view regions from the chronologically acquired data of boundary positions. That is, the non-angle-of-view region extraction processing section 45b extracts non-angle-of-view regions outside of the angle of view from the data of the boundary position B1 in the first time t1 in the past and the data of boundary positions Bp acquired until a current time tp (p=n+1 in FIG. 8).

Figure 8:
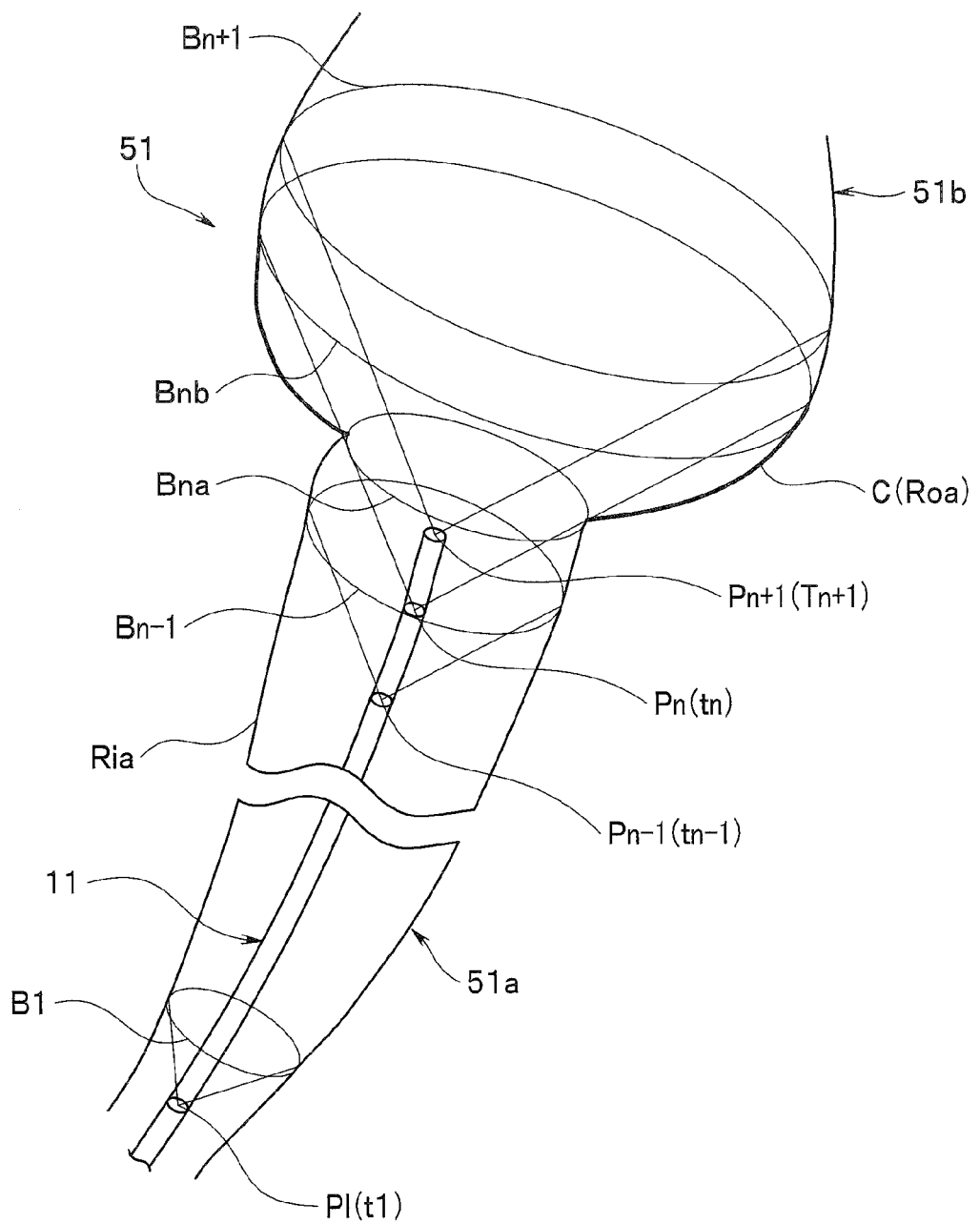
FIG. 8 is a diagram showing an example that a non-angle-of-view region is generated when images are chronologically picked up by inserting the insertion portion into the renal pelvis and renal calyces.

FIG. 8 shows a situation of observing the inside of the renal calyx 51b in a state that a region out of the boundary of the angle of view is generated. In FIG. 8, the boundary positions acquired at an observation position Pn−1 in a time tn−1, an observation position Pn in a time tn, and an observation position Pn+1 in a time tn+1 are indicated by Bn−1, Bn, and Bn+1, respectively.

The non-angle-of-view region extraction processing section 45b moves the boundary position from the boundary position B1 to the boundary position Bn+1 on the image of the renal pelvis and renal calyces 51 along a trajectory of the observation positions P1 to Pn+1. The position on the image of the renal pelvis and renal calyces 51 in the middle of the movement of the boundary position is the angle-of-view region Ria. On the other hand, a region including a curve C (Roa) indicated by a thick line in FIG. 8 is out of the angle of view, and the region is extracted as a non-angle-of-view region Roa. The non-angle-of-view region Roa formed by the curve C (Roa) is, for example, a region on the image of the renal calyx 51b between a first boundary position Bna on the image of the renal calyx 51b where a line indicating the boundary of the angle of view at the observation position Pn comes into contact in the middle and a second boundary portion Bnb in which the boundary of the angle of view reaches on the outside of the first boundary position Bna.

In the case of FIG. 8, assuming that the first boundary position Bna and the second boundary position Bnb can be approximated as an upper surface and a bottom surface of a circular cone, respectively, a region in a convex shape in which a side surface part of the cone is swelled outside is extracted as the non-angle-of-view region Roa. The shapes of the first boundary position Bna and the second boundary position Bnb are actually more complicated, and the shapes are more complicated than the non-angle-of-view region Roa.

Figure 9:
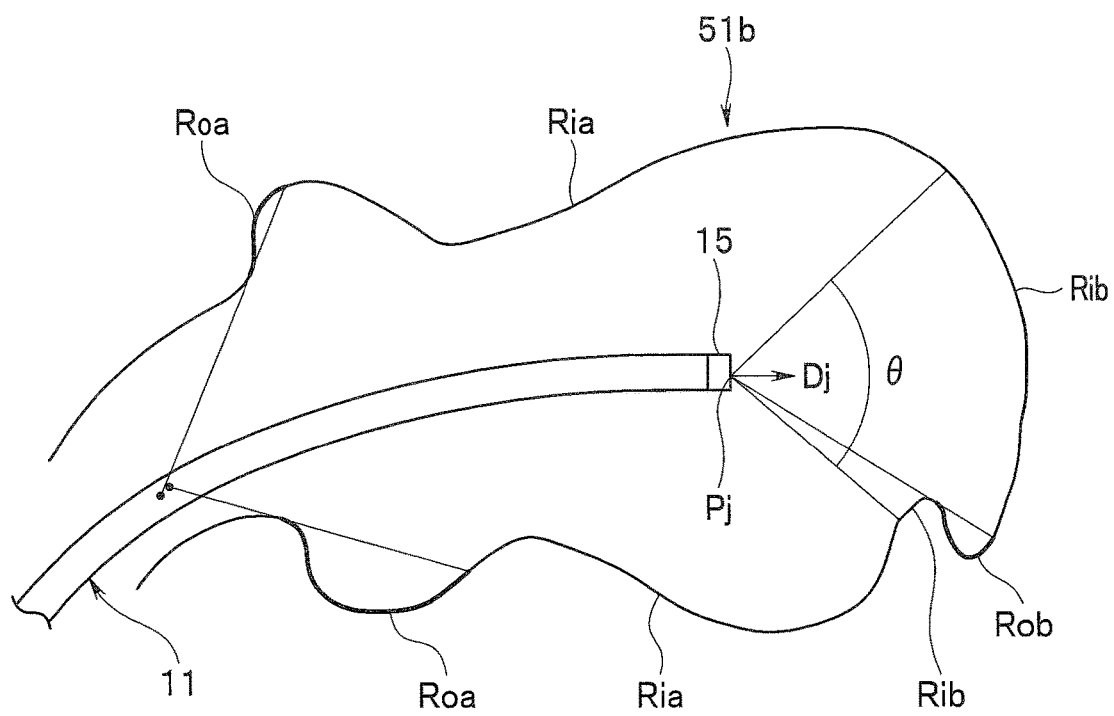
FIG. 9 is a diagram showing a situation of picking up an image of a region in the boundary of the angle of view of the image pickup section to extract angle-of-view regions and non-angle-of-view regions when a moving distance as a predetermined condition becomes equal to or smaller than a threshold.

Although the situation that the non-angle-of-view region Roa formed by the curve C (Roa) is determined by the boundary of the angle of view at the observation position Pn is described in FIG. 8, a part indicated by the curve C (Roa) is extracted at the observation position Pn, and the remaining non-angle-of-view region is extracted at one or a plurality of observation positions different from the observation position Pn in some cases, for example. FIG. 9 referenced below shows an example in which the non-angle-of-view regions Roa are respectively extracted at two slightly different observation positions. In general, the non-angle-of-view regions extracted at a plurality of observation positions are combined to determine the final non-angle-of-view region.

In next step S22 of FIG. 5B, the judgement section 47b judges whether the predetermined conditions are satisfied. More specifically, the judgement section 47b judges whether the first condition of the predetermined conditions is satisfied in step S22a. The first condition is equivalent to a) which is a condition that the moving distance from the observation position of the last time is equal to or smaller than a threshold. More specifically, the first condition is a condition for judging a state such as stop of the movement of the distal end portion 15 in a case that the observation is performed while the distal end portion 15 is moved.

If the first condition is not satisfied, the judgement section 47b judges whether the second condition is satisfied in step S22b. The second condition is equivalent to b) which is a condition of the movement reversal in which the movement direction is reversed. If the second condition is not satisfied, the judgement section 47b judges whether the third condition is satisfied in step S22c. The third condition is equivalent to c) which is a condition that the luminance values of a plurality of pixels in a set region set in the image acquired by the image pickup section 25 are equal to or greater than a luminance threshold. If the third condition is not satisfied, the judgement section 47b judges whether the fourth condition is satisfied in step S22d. The fourth condition is equivalent to d) which is a condition that the distance between the current observation position of the objective optical system 23 acquired by the information acquisition section and the three-dimensional shape of the renal pelvis and renal calyces in the visual line direction of the position is equal to or smaller than a threshold.

In a case of a judgement result satisfying at least one of the first condition, the second condition, the third condition, and the fourth condition, the non-angle-of-view region extraction processing section 45b (or the angle-of-view region extraction processing section 45d provided in the non-angle-of-view region extraction processing section 45b as shown in FIG. 2) in step S23 extracts an angle-of-view region Rib in the angle of view of the image pickup section 25 from the image of the renal pelvis and renal calyces 51 at the observation position and the visual line direction of the objective optical system 23 satisfying the condition.

In next step S24, the non-angle-of-view region extraction processing section 45b extracts, as a non-angle-of-view region Rob, a region excluding the angle-of-view region extracted in step S23 from the image of the renal pelvis and renal calyces 51.

FIG. 9 shows an explanatory diagram of the operation of the process of FIG. 5B. As shown in FIG. 9, when the distal end portion 15 of the insertion portion 11 is inserted into the renal calyx 51b, and an opposing region is blocked, the surgeon stops the operation of inserting the insertion portion 11. Therefore, the movement speed (of the insertion portion 11) decreases.

Consequently, the judgement section 47b judges that the condition of step S22a is satisfied, and the angle-of-view region Rib in an angle of view θ (indicated by a thick line) is extracted in a state of an observation position Pj and a visual line direction Dj shown in FIG. 9 satisfying the condition of step S22a. In this case, for example, a light beam vector is radially applied (emitted) in the angle of view θ of the image pickup section 25 from the observation position Pj of the objective optical system in the image pickup section 25, and a region in which the light beam vector can be applied is extracted as the angle-of-view region Rib. Note that before reaching the observation position Pj and the visual line direction Dj in FIG. 9, the non-angle-of-view regions Roa of the parts indicated by thick lines are extracted by the process described above, and the region other than the non-angle-of-view regions Roa is the angle-of-view region Ria.

A region indicated by a thick line excluding the angle-of-view region Rib extracted from the image of the renal calyx 51b (or the renal pelvis and renal calyces 51) in the angle of view θ is the non-angle-of-view region Rob.

In step S25, the non-angle-of-view region extraction processing section 45b adds the non-angle-of-view region Roa extracted in step S21 and the non-angle-of-view region Rob extracted in step S24 and sets the regions as the final non-angle-of-view regions Ro. After the process of step S25, the process moves to S11 in FIG. 5A. Note that after step S11, the non-angle-of-view regions Ro extracted in FIG. 5B are used. If the judgement result indicates that the fourth condition is not satisfied in step S22d, the process moves to step S25. In this case, the non-angle-of-view region Rob is 0, and the non-angle-of-view regions Ro are equal to the non-angle-of-view regions Roa.

According to the present embodiment with the operation, the non-angle-of-view regions Ro as unobserved regions can be extracted by image processing with a smaller amount of calculation than in a conventional example. When the inner wall of the luminal shape portion is observed while the distal end portion 15 of the endoscope 2 is moved, the data of the boundary positions that chronologically become boundaries of the angle of view can be acquired to extract the non-angle-of-view regions Ro as unobserved regions. Therefore, the non-angle-of-view regions Ro as unobserved regions can be extracted by a small amount of calculation.

According to the present embodiment, the endoscope 2 (2A or 2B) actually provided with the image pickup section 25 displays the identification image that distinguishes the angle-of-view region obtained by chronologically and optically observing the inside of the renal pelvis and renal calyces 51 as predetermined luminal organs in an endoscopic image with the angle of view of the image pickup section 25 from the unobserved non-angle-of-view region outside of the angle of view. Therefore, the user, such as a surgeon, can easily identify the region not actually observed by the endoscope, and missing of observation can be reduced to smoothly perform the endoscopy.

Although the identification image displayed as shown in FIG. 7 described above can be determined by the viewpoint position Pv, the viewpoint direction Dv, and the like set in step S9 of FIG. 5A, the identification image may be displayed in a direction with a largest non-angle-of-view region as described below.

Figure 10A:
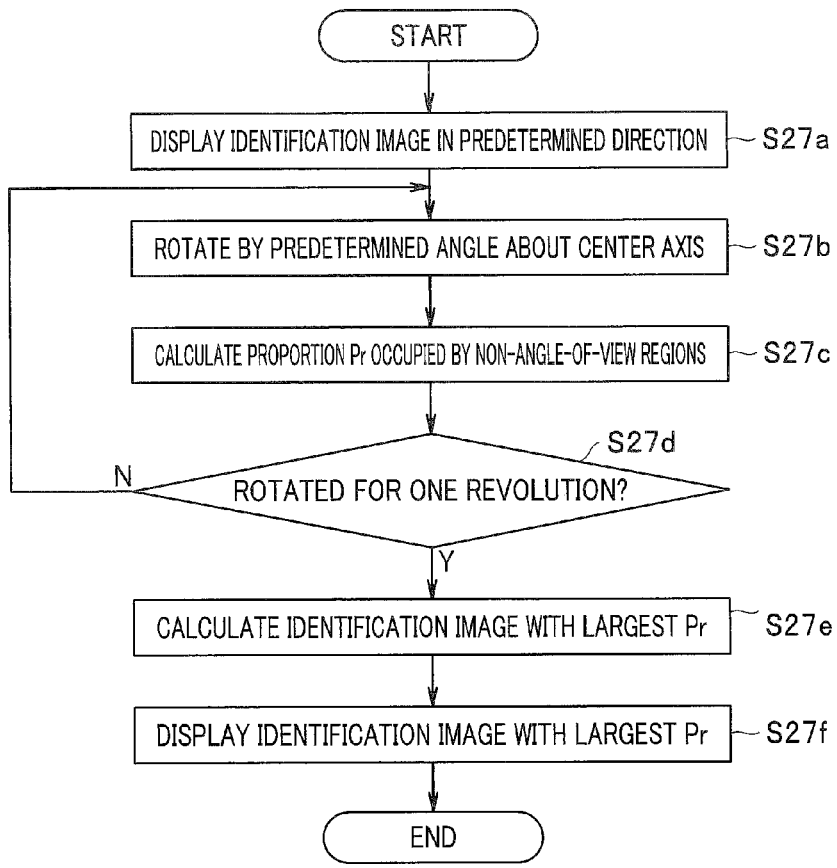
FIG. 10A is a flowchart showing an example of a process of calculating an identification image in a display direction in which a proportion of the non-angle-of-view region is the largest.

FIG. 10A shows an example of a process of generating the identification image in a direction with the largest non-angle-of-view region.

In first step S27a, the identification image generation processing section 45c displays a three-dimensional identification image as viewed in a predetermined direction as shown for example in FIG. 7. In next step S27b, the identification image generation processing section 45c sets a center axis designated from the input apparatus 49 or the like as a rotation center and rotates the identification image by a predetermined angle (for example, about 5 degrees).

In next step S27c, the identification image generation processing section 45c calculates a proportion Pr of the non-angle-of-view regions Ro in the entire identification image that can be viewed in the predetermined direction in the state that the identification image is rotated.

In next step S27d, the identification image generation processing section 45c judges whether the identification image is rotated for one revolution (360 degrees). If the identification image is not rotated for one revolution, the process returns to step S27b, and a similar process is executed. If the judgement result indicates that the identification image is rotated for one revolution, in next step S27e, the identification image generation processing section 45c calculates the identification image in which the calculated proportion Pr of the non-angle-of-view regions Ro is the largest.

In next step S27f, the identification image generation processing section 45c displays the identification image in which the calculated proportion Pr of the non-angle-of-view regions Ro is the largest and ends the process of FIG. 10A. The identification image with the maximum proportion Pr of the non-angle-of-view region Ro is displayed, and the surgeon can more easily figure out the existence of the unobserved non-angle-of-view regions Ro.

Note that the endoscopic image picked up by the image pickup section 25 is displayed in the image display area 5a substantially close to an octagon as illustrated in the monitor 5 of FIG. 1, and a size of the image display area 5a corresponds to the angle of view of the image pickup section 25. The objective optical system 23 mounted on the endoscope 2 is generally designed to be able to perform observation with a large angle of view. A distortion of image is generated on a peripheral side of the angle of view due to optical aberration, and the image quality in observation is lower on the peripheral side compared to a central side (with a small angle of view).

Figure 10B:
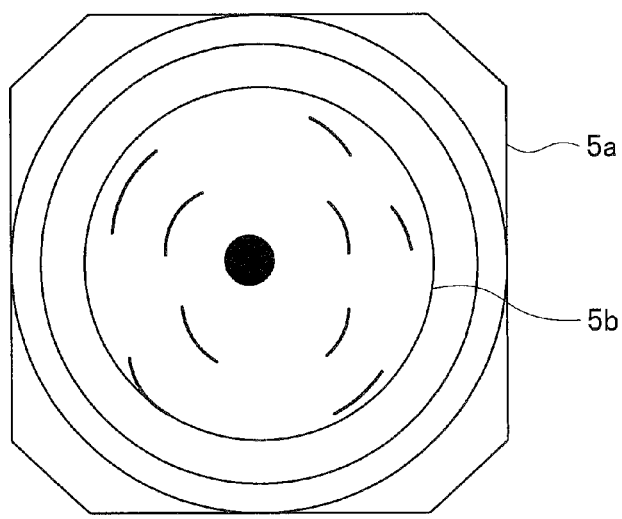
FIG. 10B is a diagram showing a situation of setting a set angle of view inside of the actual angle of view of the image pickup section.

Therefore, assuming that the angle of view of the image pickup section 25 is 100%, the user may be able to adjust or change the angle of view of the image pickup section 25 to a set angle of view with a value lower than 100% desired by the user, from the input apparatus 49, for example. FIG. 10B shows an image display area 5b corresponding to the set angle of view when the set angle of view is set from the input apparatus 49. The set angle of view set from the input apparatus 49 may be used as the angle of view used to generate the boundary position or to extract the non-angle-of-view region described above.

According to the setting of FIG. 10B, the angle-of-view region and the non-angle-of-view region in observation in a state that the image quality desired by the user is taken into account can be distinguished and displayed. Note that as shown in FIG. 10B, a plurality of image display areas (concentric circular) corresponding to a plurality of set angles of view may be displayed to allow the user to select a desirable set angle of view.

In the first embodiment described above, when, for example, the inside of one renal calyx 51b is observed by inserting the distal end portion 15 of the insertion portion 11 into the renal calyx 51b, and the angle-of-view region in the renal calyx image of the renal calyx becomes equal to or greater than a set threshold, the identification image for distinguishing the angle-of-view region and the non-angle-of-view region may be displayed.

Figure 11:
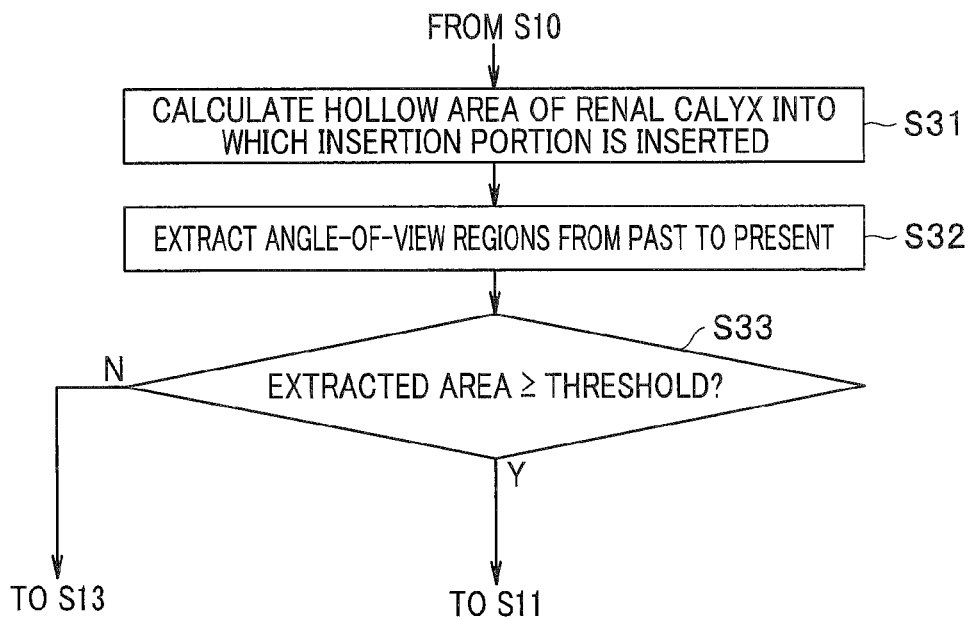
FIG. 11 is a diagram showing part of a flowchart of displaying the identification image for distinguishing the angle-of-view region and the non-angle-of-view region when the angle-of-view region becomes equal to or greater than a threshold in a case that the insertion portion is inserted into one renal calyx.

FIG. 11 shows an example of a process of this case. In step S31 after step S10 in FIG. 5A, the non-angle-of-view region extraction processing section 45b or the angle-of-view region extraction processing section 45d calculates a hollow area in one renal calyx 51b into which the distal end side of the insertion portion 11 is inserted, from the data of the renal pelvis and renal calyx image generated by the renal pelvis and renal calyx image generation section 43a.

As in the process of extracting the non-angle-of-view regions from the past boundary position to the current boundary position in step S10, the angle-of-view region extraction processing section 45d extracts, as angle-of-view regions, regions passing through the boundary positions from the past boundary position to the current boundary position in next step S32 and sends the extracted data of the angle-of-view regions to the judgement section 47b.

In next step S33, the judgement section 47b judges whether the extracted data of the angle-of-view regions is equal to or greater than a threshold set for the hollow area of the renal calyx 51b into which the insertion portion 11 is inserted. If the judgement result indicates that the data is equal to or greater than the threshold, the process proceeds to step S11 in FIG. 5A. On the other hand, if the judgement result indicates that the data is smaller than the threshold, the process moves to step S13. Note that a threshold of a proportion of the renal calyx 51b, into which the insertion portion 11 is inserted, to the hollow area may be used as the threshold. In other words, a value of the hollow area of the renal calyx 51b into which the insertion portion 11 is inserted may be standardized, and a threshold set for the standardized hollow area may be used.

Although in the description above, the viewpoint position in displaying the identification information is set outside of the renal pelvis and renal calyces 51 as luminal organs into which the insertion portion 11 of the endoscope 2 is inserted, the viewpoint position may be able to be set inside of the luminal organs.

For example, a viewpoint setting section 49b configured to selectively set the viewpoint position may be provided on the input apparatus 49 in FIG. 2, and a viewpoint position outside of the luminal organs and a viewpoint position inside of the luminal organs may be able to be selected by operation of a selection switch, a mouse, and the like forming the viewpoint setting section 49b. The setting of the viewpoint position outside of the luminal organs is already described.

On the other hand, when the viewpoint position inside of the luminal organs is selected, the viewpoint position and the viewpoint direction are further designated from the mouse or the like forming the viewpoint setting section 49b. The control section 47 controls the VBS image generation section 44a to generate a VBS image of a case that the inside of the renal pelvis and renal calyces 51 as luminal organs is observed (imaged) from the designated viewpoint position and viewpoint direction. The VBS image generation section 44a generates a corresponding VBS image, and the monitor 8 displays the generated VBS image (note that the data of the viewpoint position and the viewpoint direction designated from the input apparatus 49 may be sent to the VBS image generation section 44a without the involvement of the control section 47).

Figure 12:
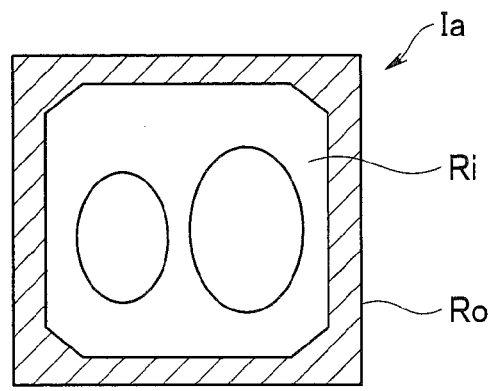
FIG. 12 is a diagram showing an example of display of a virtualized endoscopic image when the viewpoint position is set in the luminal organ.

FIG. 12 shows an example of a VBS image Ia displayed on the monitor 8, and the viewpoint position and the viewpoint direction are set to observe the renal calyx side branched from the renal pelvis side, for example.

The region in the case of observation based on the angle of view of the image pickup section 25 is the angle-of-view region Ri, and the region indicated by oblique lines outside of the angle-of-view region Ri is the non-angle-of-view region Ro. The non-angle-of-view region Ro indicated by oblique lines is, for example, colored and displayed to allow distinguishing the non-angle-of-view region Ro from the angle-of-view region Ri. Note that the angle-of-view region Ri and the non-angle-of-view region Ro in FIG. 12 are final angle-of-view region and non-angle-of-view region (including the case satisfying the predetermined condition).

In FIG. 2, a cut surface instruction input section 49c including a keyboard, a mouse, and the like for instructing a cut surface of the renal pelvis and renal calyces 51 as luminal organs may be provided on the input apparatus 49.

The control section 47 may send instruction data of the cut surface from the cut surface instruction input section 49c to the renal pelvis and renal calyx image generation section 43a, and the renal pelvis and renal calyx image generation section 43a may display a cross section of the renal pelvis and renal calyx image cut at the instructed cut surface.

Figure 13:
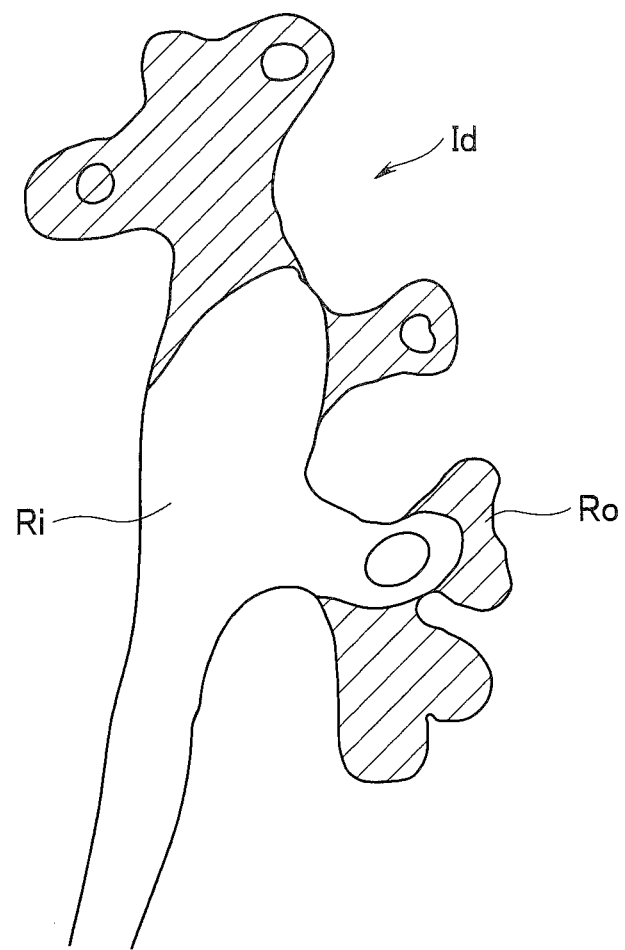
FIG. 13 is a diagram displaying the luminal organ at a cut surface and schematically displaying and projecting the angle-of-view region and the non-angle-of-view region on the cut surface.

FIG. 13 shows a cross-sectional view Id of a case that a cut surface almost parallel to the plane of paper is instructed in the renal pelvis and renal calyces 51 shown in FIG. 3, for example.

The identification image generation processing section 45c displays the non-angle-of-view region Ro by distinguishing the non-angle-of-view region Ro from the angle-of-view region Ri as indicated by, for example, oblique lines in the cross-sectional view Id. When the angle-of-view region Ri and the non-angle-of-view region Ro are distinguished by extracting an image in a hollow shape based on the cut surface, the angle-of-view region Ri and the non-angle-of-view region Ro are distinguished along a curved part on a cross section of the hollow shape. In this case, the distinction of the regions is hard to recognize. Therefore, in the example illustrated in FIG. 13, the angle-of-view region Ri and the non-angle-of-view region Ro other than the cut surface are illustrated in a state of a projection cut surface in which the regions are projected on the cut surface. In this way, the angle-of-view region Ri and the non-angle-of-view region Ro can be easily distinguished, and levels of sizes of the regions can be easily figured out.

Note that the projection cut surface may be displayed so as to easily recognize the unobserved non-angle-of-view region Ro, or the projection cut surface may be displayed to include a large amount of non-angle-of-view region Ro.

Figure 14:
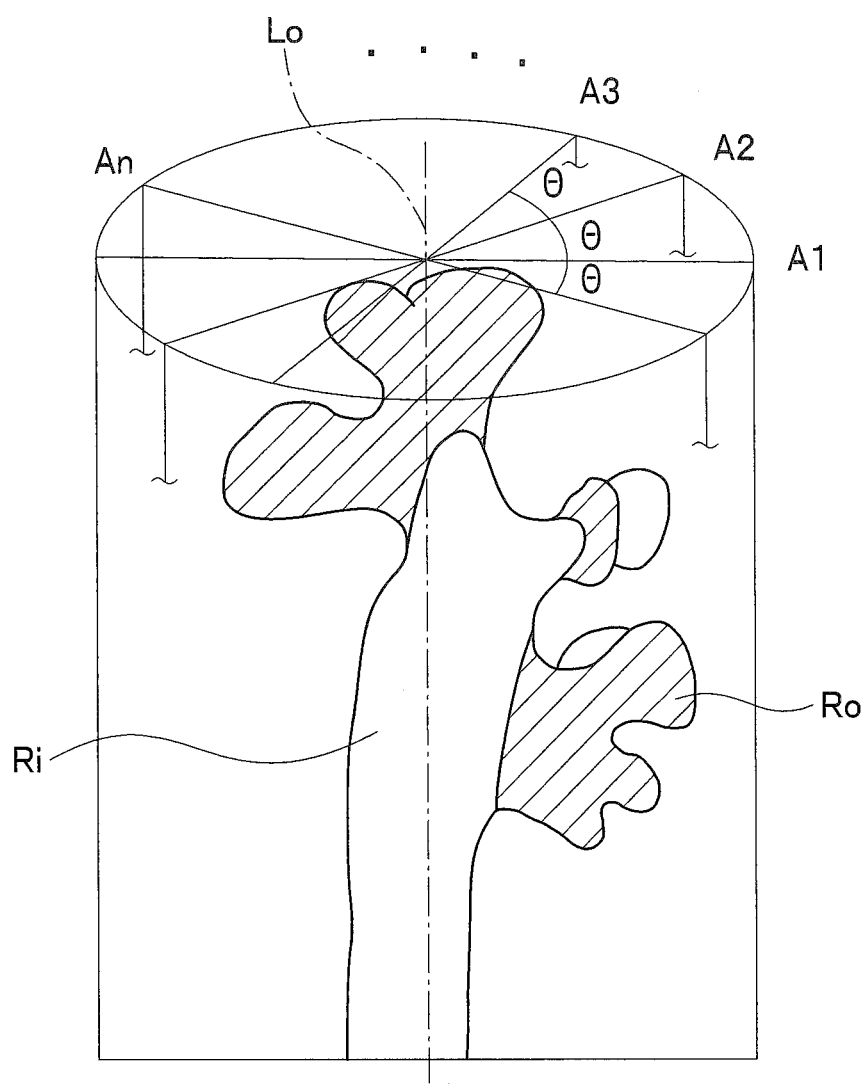
FIG. 14 is a diagram showing a situation of setting a projection cut surface for each predetermined angle including a center line in a three-dimensional identification image and displaying the angle-of-view region and the non-angle-of-view region projected on each projection cut surface.

FIG. 14 shows an explanatory diagram of a case in which the non-angle-of-view region Ro is displayed at a projection cut surface including a large amount of non-angle-of-view region Ro, as the projection cut surface on which the non-angle-of-view region Ro is projected.

For example, for the three-dimensional identification image in which the angle-of-view region Ri and the non-angle-of-view region Ro are extracted and distinguished as shown in FIG. 7, the user inputs a position and a direction of a center line Lo of the projection cut surface from the input apparatus 49 as shown in FIG. 14 and inputs a cut angle pitch θ.

In this case, a projection cut surface image generation processing section 45f provided on the identification image generation processing section 45c sequentially sets a projection cut surface A1 with an angle 0 in the three-dimensional identification image, a projection cut surface A2 with an angle θ, a projection cut surface A3 with an angle 2θ, . . . , and a projection cut surface An with an angle (n−1)×θ and projects the angle-of-view region Ri and the non-angle-of-view region Ro in the three-dimensional identification image on each projection cut surface Ai from a direction perpendicular to each projection cut surface Ai. The projection cut surface image generation processing section 45f may be provided outside of the identification image generation processing section 45c.

Next, the projection cut surface image generation processing section 45f calculates the number of pixels or the area of the non-angle-of-view region Ro on each projection cut surface Ai and specifies a projection cut surface Ak with the maximum number of pixels or area.

The projection cut surface image generation processing section 45f then displays an image of the specified projection cut surface Ak as a two-dimensional identification image in which the angle-of-view region Ri and the non-angle-of-view region Ro are distinguished.

Note that the projection cut surface may be, for example, fixed, and the three-dimensional identification image side may be sequentially rotated by the cut angle pitch θ. The angle-of-view region Ri and the non-angle-of-view region Ro projected on the fixed projection cut surface may be sequentially displayed, and the projection cut surface at a rotation angle with the maximum number of pixels or area of the non-angle-of-view region Ro may be specified. Then, the projection cut surface may be displayed.

Figure 15A:
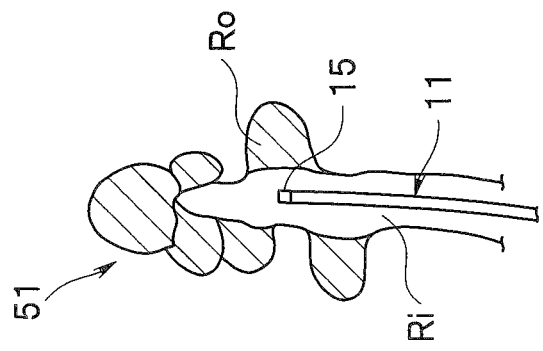
FIG. 15A is a diagram showing an example of display of the identification image in an initial state when the inside of the luminal organ is observed.
Figure 15B:
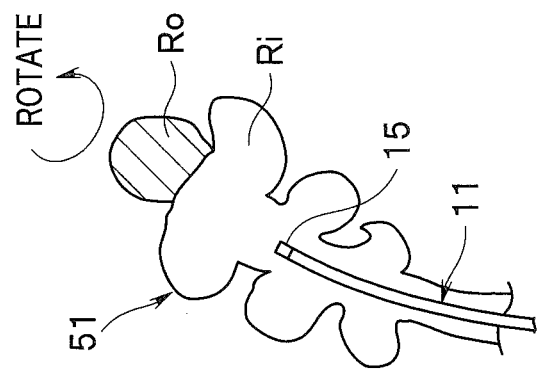
FIG. 15B is a diagram showing an example of display of the identification image when the insertion portion is inserted into a deep side in the luminal organ after FIG. 15A.
Figure 15C:
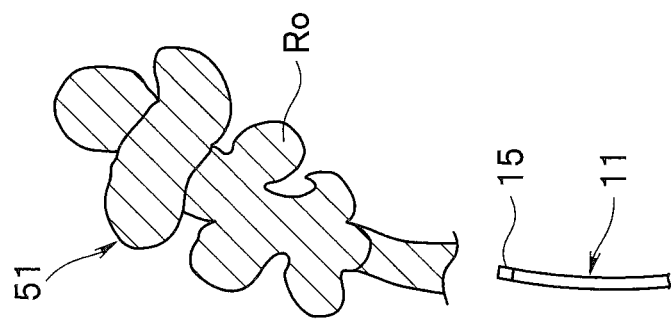
FIG. 15C is a diagram showing an example of display in which the identification image of the luminal organ is displayed from a back side after FIG. 15B.

When the insertion portion 11 is inserted into the renal pelvis and renal calyces 51 as luminal organs to chronologically display the identification image, the identification image may be displayed as schematically shown in FIGS. 15A, 15B, and 15C. For example, in initial display in the initial state before the insertion as shown in FIG. 15A, the entire image of the renal pelvis and renal calyces 51 on the front side as viewed from the abdominal side is displayed as the non-angle-of-view region Ro indicated by oblique lines in the identification image. Subsequently, the distal end portion 15 of the insertion portion 11 is inserted to the deep side to perform the observation, and most of the image of the renal pelvis and renal calyces 51 on the front side becomes the angle-of-view region Ri in the identification image as shown in FIG. 15B.

In this state, the surgeon performs instruction operation for rotating the identification image of the three-dimensional image of the renal pelvis and renal calyces 51 for 180 degrees to set a state of displaying an identification image of the renal pelvis and renal calyces 51 of the rear side as viewed from the back side. The surgeon then observes the non-angle-of-view region Ro in the identification image of the renal pelvis and renal calyces 51 on the rear side shown in FIG. 15C. In this way, the unobserved region can be efficiently observed with reference to the identification information (coloring) in the images of the renal pelvis and renal calyces 51 on the front side and the rear side.

As shown in FIG. 15B, a rotation instruction section including a keyboard and the like for performing the instruction operation for rotating the three-dimensional identification image of the renal pelvis and renal calyces 51 at an arbitrary angle, such as 180 degrees, may be provided on the input apparatus 49. The three-dimensional identification image of the renal pelvis and renal calyces 51 may be able to be rotated at a predetermined angle, such as 180 degrees, from a scope switch or the like provided on the operation portion 12 of the endoscope 2.

Note that although the case of an actual endoscope is described in the present invention, the present invention can be similarly applied to a case of using a virtualized endoscope.

Although the predetermined luminal organs are renal pelvis and renal calyces in the case described above, the description can also be applied to a case of luminal organs such as a digestive tract and a bronchus.

Note that embodiments formed by partially combining the embodiments and the like also belong to the present invention.

What is claimed is:

1. An endoscope system configured to analyze, when an endoscope is inserted into a subject, an observed region and an unobserved region of the endoscope using information of a three-dimensional image of the subject obtained in advance, the endoscope system comprising:
  one or more processors comprising hardware, wherein the one or more processors are configured to:

extract a predetermined luminal organ existing in the three-dimensional image, as a luminal organ model;

acquire information of an observation position and a visual line direction for performing observation inside the subject by using an objective optical system;

generate boundary position information indicating a boundary position of an angle-of-view region and another region of the objective optical system on the three-dimensional image of the subject based on the information of the observation position and the visual line direction that change along with temporal change observation and based on angle of view information indicating an angle of view in the observation using the objective optical system; and extract a non-angle-of-view region not in the angle of view on the three-dimensional image based on the boundary position information, wherein the processors are further configured to:

be able to three-dimensionally change a display direction for displaying the luminal organ model, and when an identification image provided with identification information is generated on the luminal organ model with the display direction changed, generate the identification image in a direction such that a proportion of the non-angle-of-view region in the identification image is largest.

2. The endoscope system according to claim 1, wherein the processors are configured to store information of the three-dimensional image.

3. The endoscope system according to claim 1, further comprising:

an image sensor configured to pick up an image of the inside of the subject, wherein the processors are configured to:

acquire information of an observation position and a visual line direction of the objective optical system included in the image sensor, align three-dimensional information of the observation position with a coordinate system of the three-dimensional image of the subject, and generate the boundary position information based on the information of the observation position and the visual line direction of the objective optical system aligned with the coordinate system of the three-dimensional image and based on image information of the inside of the subject picked up by the image sensor.

4. The endoscope system according to claim 3, wherein the processors are configured to be able to selectively switch between a first mode for displaying the identification image and a second mode for not displaying the identification image.

5. The endoscope system according to claim 3, wherein the processors are configured to generate a superimposed image in which the observation position of the objective optical system acquired is superimposed on the identification image.

6. The endoscope system according to claim 1, wherein the processors are configured to extract the non-angle-of-view region from an initial position that is the observation position in an initial state to a final position that is the observation position in a state of ending the observation.

7. The endoscope system according to claim 3, wherein the processors are configured to:

judge whether chronological movement of the objective optical system and the image of the inside of the subject acquired by the image sensor by using the objective optical system satisfy a predetermined condition; and acquire the angle of view information of the image sensor including the objective optical system judged to satisfy the predetermined condition from on a result of the judgment, extract the angle-of-view region by applying a light beam vector in the angle of view corresponding to the acquired angle of view information, and reflect the extracted angle-of-view region on the non-angle-of-view region.

8. The endoscope system according to claim 7, wherein the processors are configured to make judgment using, as the predetermined condition, one or two or more of the following conditions:

a moving distance in which a distance between an observation position of a previous time and an observation position of a current time of the objective optical system is equal to or smaller than a threshold;

movement reversal in which a movement direction of the objective optical system is reversed;

a pixel value in which a sum of luminance values of a plurality of pixels included in the subject acquired by the image sensor is equal to or greater than a threshold; and a near distance in which a distance from the observation position of the current time of the objective optical system to the three-dimensional image of the subject in a visual line direction of the observation position of the current time is equal to or smaller than a threshold.

9. The endoscope system according to claim 3, wherein the processors are configured to:

generate a virtualized endoscopic image corresponding to an endoscopic image picked up by the image sensor from the three-dimensional image based on the information of the observation position and the visual line direction of the objective optical system, and the angle of view information; and extract the boundary position information indicating a boundary of the angle of view in the generated virtualized endoscopic image from the luminal organ model.

* * * * *